(12) United States Patent
Xuan et al.

(10) Patent No.: US 10,738,288 B2
(45) Date of Patent: Aug. 11, 2020

(54) EFFICIENT PHOSPHOLIPASE C MUTANT THAT DOES NOT RELY ON ZINC IONS

(71) Applicant: Wilmar (Shanghai) Biotechnology Research & Development Center Co., Ltd., Shanghai (CN)

(72) Inventors: Yaoji Xuan, Shanghai (CN); Sitian Gu, Shanghai (CN); Wei Wu, Shanghai (CN); Sha Liu, Shanghai (CN); Yueyi Bao, Shanghai (CN); Qiwen Niu, Shanghai (CN)

(73) Assignee: Wilmar (Shanghai) Biotechnology Research & Development Center Co., Ltd., Shanghai (CN)

( * ) Notice: Subject to any disclaimer, the term of this patent is extended or adjusted under 35 U.S.C. 154(b) by 0 days.

(21) Appl. No.: 16/061,574

(22) PCT Filed: Dec. 15, 2016

(86) PCT No.: PCT/CN2016/110030
§ 371 (c)(1),
(2) Date: Jun. 12, 2018

(87) PCT Pub. No.: WO2017/101801
PCT Pub. Date: Jun. 22, 2017

(65) Prior Publication Data
US 2018/0362942 A1    Dec. 20, 2018

(30) Foreign Application Priority Data

Dec. 16, 2015 (CN) .......................... 2015 1 0946696

(51) Int. Cl.
| | | |
|---|---|---|
| *C12N 9/48* | (2006.01) | |
| *C12N 15/00* | (2006.01) | |
| *C12N 1/20* | (2006.01) | |
| *C12P 7/00* | (2006.01) | |
| *C07H 21/04* | (2006.01) | |
| *C12N 9/16* | (2006.01) | |
| *C12N 15/63* | (2006.01) | |
| *C11B 3/00* | (2006.01) | |
| *C12N 9/20* | (2006.01) | |
| *C12R 1/085* | (2006.01) | |

(52) U.S. Cl.
CPC .................. *C12N 9/16* (2013.01); *C11B 3/00* (2013.01); *C11B 3/003* (2013.01); *C12N 9/20* (2013.01); *C12N 15/63* (2013.01); *C12P 7/00* (2013.01); *C12Y 301/04003* (2013.01); *C12R 1/085* (2013.01)

(58) Field of Classification Search
None
See application file for complete search history.

(56) References Cited

U.S. PATENT DOCUMENTS

| | | | |
|---|---|---|---|
| 7,226,771 B2 | 6/2007 | Gramatikova et al. | |
| 10,144,919 B2 * | 12/2018 | Xu | ............................ C12N 9/48 |
| 2016/0362665 A1 | 12/2016 | Xu et al. | |

FOREIGN PATENT DOCUMENTS

| | | |
|---|---|---|
| CN | 101426918 A | 5/2009 |
| CN | 104630174 A | 5/2015 |
| WO | 2015017045 A1 | 3/2005 |
| WO | WO 2015/067161 * | 5/2015 |

OTHER PUBLICATIONS

Studer (Residue mutations and their impact on protein structure and function: detecting beneficial and pathogenic changes. Biochem. J. (2013) 449, 581-594.*
Gouin. iactA of Listeria ivanovii, although distantly related to *Listeria monocytogenes* actA, restores actin tail formation in an *L. monocytogenes* actA mutant.Infect Immun. Jul. 1995;63(7):2729-37.*
International Search Report for PCT/CN2016/110030 with English translation, dated Feb. 4, 2017, 7 pages.
Antikainen, Nina M., et al., "Altering Substrate Specificity of Phosphatidylcholine-Preferring Phospholipase C of *Bacillus cereus* by Random Mutagenesis of the Headgroup Binding Site", Biochemistry, vol. 42, No. 6, Jan. 18, 2003, pp. 1603-1610.
Benfield, Aaron P., et al., "Structural Studies Examining the Substrate Specificity Profiles of PC-PLCBc Protein Varients", Archives of Biochemistry and Biophysics, vol. 460, No. 1, Feb. 12, 2007, pp. 1-13.
Yu, Zhenzhen, et al., "Progress on Phospholipase C in Enzymatic Degumming Technology", China Oils and Fats, vol. 38, No. 7, Jul. 31, 2013, pp. 19-22, English translation of Abstract.

* cited by examiner

*Primary Examiner* — Yong D Pak
(74) *Attorney, Agent, or Firm* — Quarles & Brady LLP

(57) ABSTRACT

Provided is a mutant of the wild type phosphatidylcholine-specific phospholipase C of *Bacillus cereus*. The mutations involved comprise the amino acid residue at position 63 being mutated from asparagine to aspartic acid, the amino acid residue at position 131 being mutated from asparagine to serine, and the amino acid residue at position 134 being mutated from asparagine to aspartic acid, and may comprise the amino acid residue at position 56 being mutated from tyrosine to alanine, lysine, asparagine, glutamine, histidine or tryptophan, and further, may also comprise the amino acid residue at position 106 being mutated from methionine to valine. Also provided are a polynucleotide molecule encoding the mutant, a nucleic acid construct and a host cell comprising the polynucleotide molecule, a composition comprising the mutant, and the use of the mutant, the polynucleotide molecule, the nucleic acid construct and the host cell.

21 Claims, 3 Drawing Sheets
Specification includes a Sequence Listing.

SEQUENCE LISTING

```
<160> NUMBER OF SEQ ID NOS: 83

<210> SEQ ID NO 1
<211> LENGTH: 738
<212> TYPE: DNA
<213> ORGANISM: Artificial Sequence
<220> FEATURE:
<223> OTHER INFORMATION: Synthetic - Nucleotide sequence of mutant
      PLC-N63DN131SN134D

<400> SEQUENCE: 1
tggtcagctg aggacaagca taaggaaggt gtgaatagtc acttatggat cgtgaaccgt      60
gccattgata taatgtctag gaatacaact ctggttaagc aagatagagt tgctcaattg     120
aatgaatggc gtacagagct agagaatggc atctacgctg ctgattatga aaccccctat    180
tacgatgaca gtaccttcgc ttctcacttt tacgatccag acaacggaaa gacatatatc     240
ccattcgcca agcaagctaa ggagactgga gctaagtact tcaagttggc tggagagtca     300
tacaagaata aagacatgaa gcaggccttc tttatcttg ggttgtcatt gcattatttg      360
ggcgatgtca accaacctat gcatgccgca tcctttacgg acctgtccta tccacagggt     420
tttcactcca agtacgagaa ctttgtcgat actattaaag acaactacaa agttaccgat     480
gggaacggat attggaattg gaaaggcacc aaccctgaag aatggattca cggtgcagca     540
gtagttgcaa aacaggacta ctctggaatt gtcaatgaca ataccaaaga ttggttgtg     600 aaagccgcag tctcccagga atatgcagat aaatggagag ctgaagttac acctatgact     660
ggtaaacgac taatggatgc ccaaagagtt actgctggtt acattcaatt atggttcgac     720
acttacggtg acaggtaa                                                  738

<210> SEQ ID NO 2
<211> LENGTH: 245
<212> TYPE: PRT
<213> ORGANISM: Artificial Sequence
<220> FEATURE:
<223> OTHER INFORMATION: Synthetic - Amino acid sequence of mutant
      PLC-N63DN131SN134D

<400> SEQUENCE: 2

Trp Ser Ala Glu Asp Lys His Lys Glu Gly Val Asn Ser His Leu Trp
1               5                   10                  15

Ile Val Asn Arg Ala Ile Asp Ile Met Ser Arg Asn Thr Thr Leu Val
            20                  25                  30

Lys Gln Asp Arg Val Ala Gln Leu Asn Glu Trp Arg Thr Glu Leu Glu
        35                  40                  45

Asn Gly Ile Tyr Ala Ala Asp Tyr Glu Asn Pro Tyr Tyr Asp Ser
    50                  55                  60

Thr Phe Ala Ser His Phe Tyr Asp Pro Asp Asn Gly Lys Thr Tyr Ile
65                  70                  75                  80
```

```
Pro Phe Ala Lys Gln Ala Lys Glu Thr Gly Ala Lys Tyr Phe Lys Leu
                85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Ser Phe Thr Asp Leu Ser Tyr Pro Gln Gly Phe His Ser Lys
    130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Glu Trp Ile
                165                 170                 175

His Gly Ala Ala Val Val Ala Lys Gln Asp Tyr Ser Gly Ile Val Asn
            180                 185                 190

Asp Asn Thr Lys Asp Trp Phe Val Lys Ala Ala Val Ser Gln Glu Tyr
        195                 200                 205

Ala Asp Lys Trp Arg Ala Glu Val Thr Pro Met Thr Gly Lys Arg Leu
    210                 215                 220

Met Asp Ala Gln Arg Val Thr Ala Gly Tyr Ile Gln Leu Trp Phe Asp
225                 230                 235                 240

Thr Tyr Gly Asp Arg
                245

<210> SEQ ID NO 3
<211> LENGTH: 738
<212> TYPE: DNA
<213> ORGANISM: Artificial Sequence
<220> FEATURE:
<223> OTHER INFORMATION: Synthetic -Coding sequence of mutant
      PLC-N63DN131SN134D-Y56H

<400> SEQUENCE: 3
tggtcagctg aggacaagca taaggaaggt gtgaatagtc acttatggat cgtgaaccgt      60
gccattgata taatgtctag gaatacaact ctggttaagc aagatagagt tgctcaattg     120
aatgaatggc gtacagagct agagaatggc atctacgctg ctgatcatga aaacccctat     180
tacgatgaca gtaccttcgc ttctcacttt tacgatccag acaacggaaa gacatatatc     240
ccattcgcca agcaagctaa ggagactgga gctaagtact tcaagttggc tggagagtca     300
tacaagaata agacatgaa gcaggccttc ttttatcttg ggttgtcatt gcattatttg      360
ggcgatgtca accaacctat gcatgccgca tcctttacgg acctgtccta tccacagggt     420
tttcactcca gtacgagaa ctttgtcgat actattaaag acaactacaa agttaccgat      480
gggaacggat attggaattg gaaaggcacc aaccctgaag aatggattca cggtgcagca     540
gtagttgcaa acaggacta ctctggaatt gtcaatgaca ataccaaaga ttggtttgtg      600
aaagccgcag tctcccagga atatgcagat aaatggagag ctgaagttac acctatgact     660
ggtaaacgac taatggatgc ccaaagagtt actgctggtt acattcaatt atggttcgac     720
acttacggtg acaggtaa                                                   738

<210> SEQ ID NO 4
<211> LENGTH: 245
<212> TYPE: PRT
<213> ORGANISM: Artificial Sequence
<220> FEATURE:
<223> OTHER INFORMATION: Synthetic - Amino acid sequence of mutant
      PLC-N63DN131SN134D-Y56H
```

<400> SEQUENCE: 4

Trp Ser Ala Glu Asp Lys His Lys Glu Gly Val Asn Ser His Leu Trp
1               5                   10                  15
Ile Val Asn Arg Ala Ile Asp Ile Met Ser Arg Asn Thr Thr Leu Val
            20                  25                  30
Lys Gln Asp Arg Val Ala Gln Leu Asn Glu Trp Arg Thr Glu Leu Glu
        35                  40                  45
Asn Gly Ile Tyr Ala Ala Asp His Glu Asn Pro Tyr Tyr Asp Asp Ser
    50                  55                  60
Thr Phe Ala Ser His Phe Tyr Asp Pro Asp Asn Gly Lys Thr Tyr Ile
65                  70                  75                  80
Pro Phe Ala Lys Gln Ala Lys Glu Thr Gly Ala Lys Tyr Phe Lys Leu
                85                  90                  95
Ala Gly Glu Ser Tyr Lys Asn Lys Asp Met Lys Gln Ala Phe Phe Tyr
            100                 105                 110
Leu Gly Leu Ser Leu His Tyr Leu Gly Asp Val Asn Gln Pro Met His
        115                 120                 125
Ala Ala Ser Phe Thr Asp Leu Ser Tyr Pro Gln Gly Phe His Ser Lys
    130                 135                 140
Tyr Glu Asn Phe Val Asp Thr Ile Lys Asp Asn Tyr Lys Val Thr Asp
145                 150                 155                 160
Gly Asn Gly Tyr Trp Asn Trp Lys Gly Thr Asn Pro Glu Glu Trp Ile
                165                 170                 175
His Gly Ala Ala Val Val Ala Lys Gln Asp Tyr Ser Gly Ile Val Asn
            180                 185                 190
Asp Asn Thr Lys Asp Trp Phe Val Lys Ala Ala Val Ser Gln Glu Tyr
        195                 200                 205
Ala Asp Lys Trp Arg Ala Glu Val Thr Pro Met Thr Gly Lys Arg Leu
    210                 215                 220
Met Asp Ala Gln Arg Val Thr Ala Gly Tyr Ile Gln Leu Trp Phe Asp
225                 230                 235                 240
Thr Tyr Gly Asp Arg
                245

<210> SEQ ID NO 5
<211> LENGTH: 738
<212> TYPE: DNA
<213> ORGANISM: Artificial Sequence
<220> FEATURE:
<223> OTHER INFORMATION: Synthetic - Coding sequence of mutant
      PLC-N63DN131SN134D-Y56W

<400> SEQUENCE: 5
tggtcagctg aggacaagca taaggaaggt gtgaatagtc acttatggat cgtgaaccgt      60
gccattgata taatgtctag gaatacaact ctggttaagc aagatagagt tgctcaattg     120
aatgaatggc gtacagagct agagaatggc atctacgctg ctgattggga aaacccctat     180
tacgatgaca gtaccttcgc ttctcacttt tacgatccag acaacggaaa gacatatatc     240
ccattcgcca agcaagctaa ggagactgga gctaagtact tcaagttggc tggagagtca     300
tacaagaata agacatgaa gcaggccttc ttttatcttg ggttgtcatt gcattatttg     360
ggcgatgtca accaacctat gcatgccgca tcctttacgg acctgtccta tccacagggt     420
tttcactcca gtacgagaa ctttgtcgat actattaaag acaactacaa agttaccgat     480
gggaacggat attggaattg gaaaggcacc aaccctgaag aatggattca cggtgcagca     540

```
gtagttgcaa acaggacta ctctggaatt gtcaatgaca ataccaaaga ttggtttgtg    600
aaagccgcag tctcccagga atatgcagat aaatggagag ctgaagttac acctatgact    660
ggtaaacgac taatggatgc ccaaagagtt actgctggtt acattcaatt atggttcgac    720
acttacggtg acaggtaa                                                  738
```

```
<210> SEQ ID NO 6
<211> LENGTH: 245
<212> TYPE: PRT
<213> ORGANISM: Artificial Sequence
<220> FEATURE:
<223> OTHER INFORMATION: Synthetic - Amino acid sequence of mutant
      PLC-N63DN131SN134D-Y56W

<400> SEQUENCE: 6
```

| Trp | Ser | Ala | Glu | Asp | Lys | His | Lys | Glu | Gly | Val | Asn | Ser | His | Leu | Trp |
|---|---|---|---|---|---|---|---|---|---|---|---|---|---|---|---|
| 1 | | | | 5 | | | | | 10 | | | | | 15 | |

| Ile | Val | Asn | Arg | Ala | Ile | Asp | Ile | Met | Ser | Arg | Asn | Thr | Thr | Leu | Val |
|---|---|---|---|---|---|---|---|---|---|---|---|---|---|---|---|
| | | | 20 | | | | | 25 | | | | | 30 | | |

| Lys | Gln | Asp | Arg | Val | Ala | Gln | Leu | Asn | Glu | Trp | Arg | Thr | Glu | Leu | Glu |
|---|---|---|---|---|---|---|---|---|---|---|---|---|---|---|---|
| | | 35 | | | | | 40 | | | | | 45 | | | |

| Asn | Gly | Ile | Tyr | Ala | Ala | Asp | Trp | Glu | Asn | Pro | Tyr | Tyr | Asp | Asp | Ser |
|---|---|---|---|---|---|---|---|---|---|---|---|---|---|---|---|
| | 50 | | | | | 55 | | | | | 60 | | | | |

| Thr | Phe | Ala | Ser | His | Phe | Tyr | Asp | Pro | Asp | Asn | Gly | Lys | Thr | Tyr | Ile |
|---|---|---|---|---|---|---|---|---|---|---|---|---|---|---|---|
| 65 | | | | | 70 | | | | | 75 | | | | | 80 |

| Pro | Phe | Ala | Lys | Gln | Ala | Lys | Glu | Thr | Gly | Ala | Lys | Tyr | Phe | Lys | Leu |
|---|---|---|---|---|---|---|---|---|---|---|---|---|---|---|---|
| | | | | 85 | | | | | 90 | | | | | 95 | |

| Ala | Gly | Glu | Ser | Tyr | Lys | Asn | Lys | Asp | Met | Lys | Gln | Ala | Phe | Phe | Tyr |
|---|---|---|---|---|---|---|---|---|---|---|---|---|---|---|---|
| | | | 100 | | | | | 105 | | | | | 110 | | |

| Leu | Gly | Leu | Ser | Leu | His | Tyr | Leu | Gly | Asp | Val | Asn | Gln | Pro | Met | His |
|---|---|---|---|---|---|---|---|---|---|---|---|---|---|---|---|
| | | 115 | | | | | 120 | | | | | 125 | | | |

| Ala | Ala | Ser | Phe | Thr | Asp | Leu | Ser | Tyr | Pro | Gln | Gly | Phe | His | Ser | Lys |
|---|---|---|---|---|---|---|---|---|---|---|---|---|---|---|---|
| | 130 | | | | | 135 | | | | | 140 | | | | |

| Tyr | Glu | Asn | Phe | Val | Asp | Thr | Ile | Lys | Asp | Asn | Tyr | Lys | Val | Thr | Asp |
|---|---|---|---|---|---|---|---|---|---|---|---|---|---|---|---|
| 145 | | | | | 150 | | | | | 155 | | | | | 160 |

| Gly | Asn | Gly | Tyr | Trp | Asn | Trp | Lys | Gly | Thr | Asn | Pro | Glu | Glu | Trp | Ile |
|---|---|---|---|---|---|---|---|---|---|---|---|---|---|---|---|
| | | | | 165 | | | | | 170 | | | | | 175 | |

| His | Gly | Ala | Ala | Val | Val | Ala | Lys | Gln | Asp | Tyr | Ser | Gly | Ile | Val | Asn |
|---|---|---|---|---|---|---|---|---|---|---|---|---|---|---|---|
| | | | 180 | | | | | 185 | | | | | 190 | | |

| Asp | Asn | Thr | Lys | Asp | Trp | Phe | Val | Lys | Ala | Ala | Val | Ser | Gln | Glu | Tyr |
|---|---|---|---|---|---|---|---|---|---|---|---|---|---|---|---|
| | | 195 | | | | | 200 | | | | | 205 | | | |

| Ala | Asp | Lys | Trp | Arg | Ala | Glu | Val | Thr | Pro | Met | Thr | Gly | Lys | Arg | Leu |
|---|---|---|---|---|---|---|---|---|---|---|---|---|---|---|---|
| | 210 | | | | | 215 | | | | | 220 | | | | |

| Met | Asp | Ala | Gln | Arg | Val | Thr | Ala | Gly | Tyr | Ile | Gln | Leu | Trp | Phe | Asp |
|---|---|---|---|---|---|---|---|---|---|---|---|---|---|---|---|
| 225 | | | | | 230 | | | | | 235 | | | | | 240 |

| Thr | Tyr | Gly | Asp | Arg |
|---|---|---|---|---|
| | | | | 245 |

```
<210> SEQ ID NO 7
<211> LENGTH: 245
<212> TYPE: PRT
<213> ORGANISM: Artificial Sequence
<220> FEATURE:
<223> OTHER INFORMATION: Synthetic - Amino acid sequence of mutant
      PLC-N63DN131SN134D at position 56
```

```
<220> FEATURE:
<221> NAME/KEY: misc_feature
<222> LOCATION: (56)..(56)
<223> OTHER INFORMATION: Xaa is Tyr, Ala, Lys, Asn, Gln, His, Phe, Arg,
      Ser, Thr or Trp

<400> SEQUENCE: 7

Trp Ser Ala Glu Asp Lys His Lys Glu Gly Val Asn Ser His Leu Trp
1               5                   10                  15

Ile Val Asn Arg Ala Ile Asp Ile Met Ser Arg Asn Thr Thr Leu Val
            20                  25                  30

Lys Gln Asp Arg Val Ala Gln Leu Asn Glu Trp Arg Thr Glu Leu Glu
        35                  40                  45

Asn Gly Ile Tyr Ala Ala Asp Xaa Glu Asn Pro Tyr Tyr Asp Asp Ser
    50                  55                  60

Thr Phe Ala Ser His Phe Tyr Asp Pro Asp Asn Gly Lys Thr Tyr Ile
65                  70                  75                  80

Pro Phe Ala Lys Gln Ala Lys Glu Thr Gly Ala Lys Tyr Phe Lys Leu
                85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Ser Phe Thr Asp Leu Ser Tyr Pro Gln Gly Phe His Ser Lys
    130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Glu Trp Ile
                165                 170                 175

His Gly Ala Ala Val Val Ala Lys Gln Asp Tyr Ser Gly Ile Val Asn
            180                 185                 190

Asp Asn Thr Lys Asp Trp Phe Val Lys Ala Ala Val Ser Gln Glu Tyr
        195                 200                 205

Ala Asp Lys Trp Arg Ala Glu Val Thr Pro Met Thr Gly Lys Arg Leu
    210                 215                 220

Met Asp Ala Gln Arg Val Thr Ala Gly Tyr Ile Gln Leu Trp Phe Asp
225                 230                 235                 240

Thr Tyr Gly Asp Arg
                245

<210> SEQ ID NO 8
<211> LENGTH: 738
<212> TYPE: DNA
<213> ORGANISM: Artificial Sequence
<220> FEATURE:
<223> OTHER INFORMATION: Synthetic - DNA sequence designed according to
      the mature peptide sequence of Bacillus cereus
      phosphatidylcholine-specific phospholipase C and Pichia codon
      preference

<400> SEQUENCE: 8
tggtcagctg aggacaagca taaggaaggt gtgaatagtc acttatggat cgtgaaccgt      60
gccattgata taatgtctag gaatacaact ctggttaagc aagatagagt tgctcaattg     120
aatgaatggc gtacagagct agagaatggc atctacgctg ctgattatga aaacccctat     180
tacgataaca gtaccttcgc ttctcacttt tacgatccag acaacggaaa gacatatatc     240
ccattcgcca agcaagctaa ggagactgga gctaagtact tcaagttggc tggagagtca     300
```

```
tacaagaata aagacatgaa gcaggccttc ttttatcttg ggttgtcatt gcattatttg    360
ggcgatgtca accaacctat gcatgccgca aactttacga acctgtccta tccacagggt    420
tttcactcca agtacgagaa ctttgtcgat actattaaag acaactacaa agttaccgat    480
gggaacggat attggaattg gaaaggcacc aaccctgaag aatggattca cggtgcagca    540
gtagttgcaa acaggactac tctggaattg tcaatgaca ataccaaaga ttggtttgtg     600
aaagccgcag tctcccagga atatgcagat aaatggagag ctgaagttac acctatgact    660
ggtaaacgac taatggatgc ccaaagagtt actgctggtt acattcaatt atggttcgac    720
acttacggtg acaggtaa                                                 738
```

<210> SEQ ID NO 9
<211> LENGTH: 245
<212> TYPE: PRT
<213> ORGANISM: Artificial Sequence
<220> FEATURE:
<223> OTHER INFORMATION: Synthetic - Amino acid sequence designed according to the mature peptide sequence of Bacillus cereus phosphatidylcholine-specific phospholipase C and Pichia codon preference

<400> SEQUENCE: 9

```
Trp Ser Ala Glu Asp Lys His Lys Glu Gly Val Asn Ser His Leu Trp
1               5                   10                  15

Ile Val Asn Arg Ala Ile Asp Ile Met Ser Arg Asn Thr Thr Leu Val
            20                  25                  30

Lys Gln Asp Arg Val Ala Gln Leu Asn Glu Trp Arg Thr Glu Leu Glu
        35                  40                  45

Asn Gly Ile Tyr Ala Ala Asp Tyr Glu Asn Pro Tyr Tyr Asp Asn Ser
    50                  55                  60

Thr Phe Ala Ser His Phe Tyr Asp Pro Asp Asn Gly Lys Thr Tyr Ile
65                  70                  75                  80

Pro Phe Ala Lys Gln Ala Lys Glu Thr Gly Ala Lys Tyr Phe Lys Leu
                85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Asn Phe Thr Asn Leu Ser Tyr Pro Gln Gly Phe His Ser Lys
    130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Glu Trp Ile
                165                 170                 175

His Gly Ala Ala Val Val Ala Lys Gln Asp Tyr Ser Gly Ile Val Asn
            180                 185                 190

Asp Asn Thr Lys Asp Trp Phe Val Lys Ala Ala Val Ser Gln Glu Tyr
        195                 200                 205

Ala Asp Lys Trp Arg Ala Glu Val Thr Pro Met Thr Gly Lys Arg Leu
    210                 215                 220

Met Asp Ala Gln Arg Val Thr Ala Gly Tyr Ile Gln Leu Trp Phe Asp
225                 230                 235                 240

Thr Tyr Gly Asp Arg
                245
```

<210> SEQ ID NO 10
<211> LENGTH: 1012
<212> TYPE: DNA
<213> ORGANISM: Artificial Sequence
<220> FEATURE:
<223> OTHER INFORMATION: Synthetic - alpha-BC-PC-PLC DNA sequence with fused alpha factor signal peptide sequence and a Pichia Kozak sequence

<400> SEQUENCE: 10

```
cgaaacgatg agatttcctt caattttttac tgcagtttta ttcgcagcat cctccgcatt      60
agctgctcca gtcaacacta aacagaaga tgaaacggca caaattccgg ctgaagctgt       120
catcggttac tcagatttag aaggggattt cgatgttgct gttttgccat tttccaacag      180
cacaaataac gggttattgt ttataaatac tactattgcc agcattgctg ctaaagaaga      240
aggggtatct cttgagaaaa gagaggctga agcttggtca gctgaggaca agcataagga      300
aggtgtgaat agtcacttat ggatcgtgaa ccgtgccatt gatataatgt ctaggaatac      360
aactctggtt aagcaagata gagttgctca attgaatgaa tggcgtacag agctagagaa      420
tggcatctac gctgctgatt atgaaaaccc ctattacgat aacagtacct tcgcttctca      480
ctttttacgat ccagacaacg aaagacata tatcccattc gccaagcaag ctaaggagac      540
tggagctaag tacttcaagt tggctggaga gtcatacaag aataaagaca tgaagcaggc      600
cttctttttat cttgggttgt cattgcatta tttgggcgat gtcaaccaac ctatgcatgc      660
cgcaaacttt acgaacctgt cctatccaca gggttttcac tccaagtacg agaactttgt      720
cgatactatt aaagacaact acaaagttac cgatgggaac ggatattgga attggaaagg      780
caccaacct gaagaatgga ttcacggtgc agcagtagtt gcaaacagg actactctgg      840
aattgtcaat gacaatacca aagattggtt tgtgaaagcc gcagtctccc aggaatatgc      900
agataaatgg agagctgaag ttacacctat gactggtaaa cgactaatgg atgcccaaag      960
agttactgct ggttacattc aattatggtt cgacacttac ggtgacaggt aa             1012
```

<210> SEQ ID NO 11
<211> LENGTH: 35
<212> TYPE: DNA
<213> ORGANISM: Artificial Sequence
<220> FEATURE:
<223> OTHER INFORMATION: Synthetic - Primer

<400> SEQUENCE: 11

```
ccggacgtcg ctagcagatc taacatccaa agacg                                  35
```

<210> SEQ ID NO 12
<211> LENGTH: 37
<212> TYPE: DNA
<213> ORGANISM: Artificial Sequence
<220> FEATURE:
<223> OTHER INFORMATION: Synthetic - Primer

<400> SEQUENCE: 12

```
tcatcgtttc gcctaggatc cttcgaataa ttagttg                                37
```

<210> SEQ ID NO 13
<211> LENGTH: 30
<212> TYPE: DNA
<213> ORGANISM: Artificial Sequence
<220> FEATURE:
<223> OTHER INFORMATION: Synthetic - Primer

```
<400> SEQUENCE: 13
gatcctaggc gaaacgatga gatttccttc                                    30

<210> SEQ ID NO 14
<211> LENGTH: 26
<212> TYPE: DNA
<213> ORGANISM: Artificial Sequence
<220> FEATURE:
<223> OTHER INFORMATION: Synthetic - Primer

<400> SEQUENCE: 14
ccggaattct tacctgtcac cgtaag                                        26

<210> SEQ ID NO 15
<211> LENGTH: 35
<212> TYPE: DNA
<213> ORGANISM: Artificial Sequence
<220> FEATURE:
<223> OTHER INFORMATION: Synthetic - Primer

<400> SEQUENCE: 15
gttaaaatca aaacgttgtc aattggaacc agtcg                              35

<210> SEQ ID NO 16
<211> LENGTH: 40
<212> TYPE: DNA
<213> ORGANISM: Artificial Sequence
<220> FEATURE:
<223> OTHER INFORMATION: Synthetic - Primer

<400> SEQUENCE: 16
ccaattgaca acgttgattt taacgacttt taacgacaac                         40

<210> SEQ ID NO 17
<211> LENGTH: 22
<212> TYPE: DNA
<213> ORGANISM: Artificial Sequence
<220> FEATURE:
<223> OTHER INFORMATION: Synthetic - Primer

<400> SEQUENCE: 17
cgactggttc caattgacaa cg                                            22

<210> SEQ ID NO 18
<211> LENGTH: 24
<212> TYPE: DNA
<213> ORGANISM: Artificial Sequence
<220> FEATURE:
<223> OTHER INFORMATION: Synthetic - Primer

<400> SEQUENCE: 18
ggcaaatggc attctgacat cctc                                          24

<210> SEQ ID NO 19
<211> LENGTH: 23
<212> TYPE: DNA
<213> ORGANISM: Artificial Sequence
<220> FEATURE:
<223> OTHER INFORMATION: Synthetic - Primer

<400> SEQUENCE: 19
cccaagcttg gtcagctgag gac                                           23
```

```
<210> SEQ ID NO 20
<211> LENGTH: 24
<212> TYPE: DNA
<213> ORGANISM: Artificial Sequence
<220> FEATURE:
<223> OTHER INFORMATION: Synthetic - Primer

<400> SEQUENCE: 20
ccggaattct tacctgtcac cgta                                          24

<210> SEQ ID NO 21
<211> LENGTH: 37
<212> TYPE: DNA
<213> ORGANISM: Artificial Sequence
<220> FEATURE:
<223> OTHER INFORMATION: Synthetic - Primer

<400> SEQUENCE: 21
cgaaggtact gtcatcgtaa tagggttttt cataatc                            37

<210> SEQ ID NO 22
<211> LENGTH: 31
<212> TYPE: DNA
<213> ORGANISM: Artificial Sequence
<220> FEATURE:
<223> OTHER INFORMATION: Synthetic - Primer

<400> SEQUENCE: 22
ctattacgat gacagtacct tcgcttctca c                                  31

<210> SEQ ID NO 23
<211> LENGTH: 38
<212> TYPE: DNA
<213> ORGANISM: Artificial Sequence
<220> FEATURE:
<223> OTHER INFORMATION: Synthetic - Primer

<400> SEQUENCE: 23
acaggtccgt aaaggatgcg gcatgcatag gttggttg                           38

<210> SEQ ID NO 24
<211> LENGTH: 40
<212> TYPE: DNA
<213> ORGANISM: Artificial Sequence
<220> FEATURE:
<223> OTHER INFORMATION: Synthetic - Primer

<400> SEQUENCE: 24
cgcatccttt acggacctgt cctatccaca gggttttcac                         40

<210> SEQ ID NO 25
<211> LENGTH: 35
<212> TYPE: DNA
<213> ORGANISM: Artificial Sequence
<220> FEATURE:
<223> OTHER INFORMATION: Synthetic - Primer

<400> SEQUENCE: 25
gcctgcttca cgtctttatt cttgtatgac tctcc                              35

<210> SEQ ID NO 26
<211> LENGTH: 32
<212> TYPE: DNA
<213> ORGANISM: Artificial Sequence
<220> FEATURE:
<223> OTHER INFORMATION: Synthetic - Primer
```

```
<400> SEQUENCE: 26
gaataaagac gtgaagcagg ccttcttta tc                              32

<210> SEQ ID NO 27
<211> LENGTH: 30
<212> TYPE: DNA
<213> ORGANISM: Artificial Sequence
<220> FEATURE:
<223> OTHER INFORMATION: Synthetic - Primer

<400> SEQUENCE: 27
gggttttcgg catcagcagc gtagatgcca                                30

<210> SEQ ID NO 28
<211> LENGTH: 33
<212> TYPE: DNA
<213> ORGANISM: Artificial Sequence
<220> FEATURE:
<223> OTHER INFORMATION: Synthetic - Primer

<400> SEQUENCE: 28
gctgctgatg ccgaaaaccc ctattacgat gac                            33

<210> SEQ ID NO 29
<211> LENGTH: 30
<212> TYPE: DNA
<213> ORGANISM: Artificial Sequence
<220> FEATURE:
<223> OTHER INFORMATION: Synthetic - Primer

<400> SEQUENCE: 29
gggttttcgc aatcagcagc gtagatgcca                                30

<210> SEQ ID NO 30
<211> LENGTH: 33
<212> TYPE: DNA
<213> ORGANISM: Artificial Sequence
<220> FEATURE:
<223> OTHER INFORMATION: Synthetic - Primer

<400> SEQUENCE: 30
gctgctgatt gcgaaaaccc ctattacgat gac                            33

<210> SEQ ID NO 31
<211> LENGTH: 30
<212> TYPE: DNA
<213> ORGANISM: Artificial Sequence
<220> FEATURE:
<223> OTHER INFORMATION: Synthetic - Primer

<400> SEQUENCE: 31
gggttttcgt catcagcagc gtagatgcca                                30

<210> SEQ ID NO 32
<211> LENGTH: 33
<212> TYPE: DNA
<213> ORGANISM: Artificial Sequence
<220> FEATURE:
<223> OTHER INFORMATION: Synthetic - Primer

<400> SEQUENCE: 32
gctgctgatg acgaaaaccc ctattacgat gac                            33
```

-continued

<210> SEQ ID NO 33
<211> LENGTH: 30
<212> TYPE: DNA
<213> ORGANISM: Artificial Sequence
<220> FEATURE:
<223> OTHER INFORMATION: Synthetic - Primer

<400> SEQUENCE: 33
gggttttcct catcagcagc gtagatgcca                                    30

<210> SEQ ID NO 34
<211> LENGTH: 33
<212> TYPE: DNA
<213> ORGANISM: Artificial Sequence
<220> FEATURE:
<223> OTHER INFORMATION: Synthetic - Primer

<400> SEQUENCE: 34
gctgctgatg aggaaaaccc ctattacgat gac                                33

<210> SEQ ID NO 35
<211> LENGTH: 30
<212> TYPE: DNA
<213> ORGANISM: Artificial Sequence
<220> FEATURE:
<223> OTHER INFORMATION: Synthetic - Primer

<400> SEQUENCE: 35
gggttttcga atcagcagc gtagatgcca                                     30

<210> SEQ ID NO 36
<211> LENGTH: 33
<212> TYPE: DNA
<213> ORGANISM: Artificial Sequence
<220> FEATURE:
<223> OTHER INFORMATION: Synthetic - Primer

<400> SEQUENCE: 36
gctgctgatt tcgaaaaccc ctattacgat gac                                33

<210> SEQ ID NO 37
<211> LENGTH: 30
<212> TYPE: DNA
<213> ORGANISM: Artificial Sequence
<220> FEATURE:
<223> OTHER INFORMATION: Synthetic - Primer

<400> SEQUENCE: 37
gggttttcac catcagcagc gtagatgcca                                    30

<210> SEQ ID NO 38
<211> LENGTH: 33
<212> TYPE: DNA
<213> ORGANISM: Artificial Sequence
<220> FEATURE:
<223> OTHER INFORMATION: Synthetic - Primer

<400> SEQUENCE: 38
gctgctgatg gtgaaaaccc ctattacgat gac                                33

<210> SEQ ID NO 39
<211> LENGTH: 30
<212> TYPE: DNA
<213> ORGANISM: Artificial Sequence
<220> FEATURE:
<223> OTHER INFORMATION: Synthetic - Primer

```
<400> SEQUENCE: 39
ggttttcatg atcagcagcg tagatgccat                                    30

<210> SEQ ID NO 40
<211> LENGTH: 34
<212> TYPE: DNA
<213> ORGANISM: Artificial Sequence
<220> FEATURE:
<223> OTHER INFORMATION: Synthetic - Primer

<400> SEQUENCE: 40
cgctgctgat catgaaaacc cctattacga tgac                               34

<210> SEQ ID NO 41
<211> LENGTH: 30
<212> TYPE: DNA
<213> ORGANISM: Artificial Sequence
<220> FEATURE:
<223> OTHER INFORMATION: Synthetic - Primer

<400> SEQUENCE: 41
gggttttcga tatcagcagc gtagatgcca                                    30

<210> SEQ ID NO 42
<211> LENGTH: 33
<212> TYPE: DNA
<213> ORGANISM: Artificial Sequence
<220> FEATURE:
<223> OTHER INFORMATION: Synthetic - Primer

<400> SEQUENCE: 42
gctgctgata tcgaaaaccc ctattacgat gac                                33

<210> SEQ ID NO 43
<211> LENGTH: 33
<212> TYPE: DNA
<213> ORGANISM: Artificial Sequence
<220> FEATURE:
<223> OTHER INFORMATION: Synthetic - Primer

<400> SEQUENCE: 43
aggggttttc cttatcagca gcgtagatgc cat                                33

<210> SEQ ID NO 44
<211> LENGTH: 34
<212> TYPE: DNA
<213> ORGANISM: Artificial Sequence
<220> FEATURE:
<223> OTHER INFORMATION: Synthetic - Primer

<400> SEQUENCE: 44
cgctgctgat aaggaaaacc cctattacga tgac                               34

<210> SEQ ID NO 45
<211> LENGTH: 30
<212> TYPE: DNA
<213> ORGANISM: Artificial Sequence
<220> FEATURE:
<223> OTHER INFORMATION: Synthetic - Primer

<400> SEQUENCE: 45
gggttttcca atcagcagc gtagatgcca                                     30
```

```
<210> SEQ ID NO 46
<211> LENGTH: 33
<212> TYPE: DNA
<213> ORGANISM: Artificial Sequence
<220> FEATURE:
<223> OTHER INFORMATION: Synthetic - Primer

<400> SEQUENCE: 46
gctgctgatt tggaaaaccc ctattacgat gac                              33

<210> SEQ ID NO 47
<211> LENGTH: 30
<212> TYPE: DNA
<213> ORGANISM: Artificial Sequence
<220> FEATURE:
<223> OTHER INFORMATION: Synthetic - Primer

<400> SEQUENCE: 47
gggttttcca tatcagcagc gtagatgcca                                  30

<210> SEQ ID NO 48
<211> LENGTH: 33
<212> TYPE: DNA
<213> ORGANISM: Artificial Sequence
<220> FEATURE:
<223> OTHER INFORMATION: Synthetic - Primer

<400> SEQUENCE: 48
gctgctgata tggaaaaccc ctattacgat gac                              33

<210> SEQ ID NO 49
<211> LENGTH: 30
<212> TYPE: DNA
<213> ORGANISM: Artificial Sequence
<220> FEATURE:
<223> OTHER INFORMATION: Synthetic - Primer

<400> SEQUENCE: 49
ggttttcgtt atcagcagcg tagatgccat                                  30

<210> SEQ ID NO 50
<211> LENGTH: 34
<212> TYPE: DNA
<213> ORGANISM: Artificial Sequence
<220> FEATURE:
<223> OTHER INFORMATION: Synthetic - Primer

<400> SEQUENCE: 50
cgctgctgat aacgaaaacc cctattacga tgac                             34

<210> SEQ ID NO 51
<211> LENGTH: 30
<212> TYPE: DNA
<213> ORGANISM: Artificial Sequence
<220> FEATURE:
<223> OTHER INFORMATION: Synthetic - Primer

<400> SEQUENCE: 51
gggttttctg gatcagcagc gtagatgcca                                  30

<210> SEQ ID NO 52
<211> LENGTH: 33
<212> TYPE: DNA
<213> ORGANISM: Artificial Sequence
<220> FEATURE:
<223> OTHER INFORMATION: Synthetic - Primer
```

-continued

<400> SEQUENCE: 52
gctgctgatc cagaaaaccc ctattacgat gac            33

<210> SEQ ID NO 53
<211> LENGTH: 30
<212> TYPE: DNA
<213> ORGANISM: Artificial Sequence
<220> FEATURE:
<223> OTHER INFORMATION: Synthetic - Primer

<400> SEQUENCE: 53
gggttttctt gatcagcagc gtagatgcca            30

<210> SEQ ID NO 54
<211> LENGTH: 33
<212> TYPE: DNA
<213> ORGANISM: Artificial Sequence
<220> FEATURE:
<223> OTHER INFORMATION: Synthetic - Primer

<400> SEQUENCE: 54
gctgctgatc aagaaaaccc ctattacgat gac            33

<210> SEQ ID NO 55
<211> LENGTH: 33
<212> TYPE: DNA
<213> ORGANISM: Artificial Sequence
<220> FEATURE:
<223> OTHER INFORMATION: Synthetic - Primer

<400> SEQUENCE: 55
aggggttttc tctatcagca gcgtagatgc cat            33

<210> SEQ ID NO 56
<211> LENGTH: 34
<212> TYPE: DNA
<213> ORGANISM: Artificial Sequence
<220> FEATURE:
<223> OTHER INFORMATION: Synthetic - Primer

<400> SEQUENCE: 56
cgctgctgat agagaaaacc cctattacga tgac            34

<210> SEQ ID NO 57
<211> LENGTH: 30
<212> TYPE: DNA
<213> ORGANISM: Artificial Sequence
<220> FEATURE:
<223> OTHER INFORMATION: Synthetic - Primer

<400> SEQUENCE: 57
ggttttcaga atcagcagcg tagatgccat            30

<210> SEQ ID NO 58
<211> LENGTH: 34
<212> TYPE: DNA
<213> ORGANISM: Artificial Sequence
<220> FEATURE:
<223> OTHER INFORMATION: Synthetic - Primer

<400> SEQUENCE: 58
cgctgctgat tctgaaaacc cctattacga tgac            34

```
<210> SEQ ID NO 59
<211> LENGTH: 30
<212> TYPE: DNA
<213> ORGANISM: Artificial Sequence
<220> FEATURE:
<223> OTHER INFORMATION: Synthetic - Primer

<400> SEQUENCE: 59
gggttttcgg tatcagcagc gtagatgcca                                    30

<210> SEQ ID NO 60
<211> LENGTH: 33
<212> TYPE: DNA
<213> ORGANISM: Artificial Sequence
<220> FEATURE:
<223> OTHER INFORMATION: Synthetic - Primer

<400> SEQUENCE: 60
gctgctgata ccgaaaaccc ctattacgat gac                                33

<210> SEQ ID NO 61
<211> LENGTH: 30
<212> TYPE: DNA
<213> ORGANISM: Artificial Sequence
<220> FEATURE:
<223> OTHER INFORMATION: Synthetic - Primer

<400> SEQUENCE: 61
gggttttcga catcagcagc gtagatgcca                                    30

<210> SEQ ID NO 62
<211> LENGTH: 33
<212> TYPE: DNA
<213> ORGANISM: Artificial Sequence
<220> FEATURE:
<223> OTHER INFORMATION: Synthetic - Primer

<400> SEQUENCE: 62
gctgctgatg tcgaaaaccc ctattacgat gac                                33

<210> SEQ ID NO 63
<211> LENGTH: 30
<212> TYPE: DNA
<213> ORGANISM: Artificial Sequence
<220> FEATURE:
<223> OTHER INFORMATION: Synthetic - Primer

<400> SEQUENCE: 63
gggttttccc aatcagcagc gtagatgcca                                    30

<210> SEQ ID NO 64
<211> LENGTH: 33
<212> TYPE: DNA
<213> ORGANISM: Artificial Sequence
<220> FEATURE:
<223> OTHER INFORMATION: Synthetic - Primer

<400> SEQUENCE: 64
gctgctgatt gggaaaaccc ctattacgat gac                                33

<210> SEQ ID NO 65
<211> LENGTH: 33
<212> TYPE: DNA
<213> ORGANISM: Artificial Sequence
<220> FEATURE:
<223> OTHER INFORMATION: Synthetic - Primer
```

```
<400> SEQUENCE: 65
tatcaatggc atggttcacg atccataagt gac                               33

<210> SEQ ID NO 66
<211> LENGTH: 35
<212> TYPE: DNA
<213> ORGANISM: Artificial Sequence
<220> FEATURE:
<223> OTHER INFORMATION: Synthetic - Primer

<400> SEQUENCE: 66
ggatcgtgaa ccatgccatt gatataatgt ctagg                             35

<210> SEQ ID NO 67
<211> LENGTH: 37
<212> TYPE: DNA
<213> ORGANISM: Artificial Sequence
<220> FEATURE:
<223> OTHER INFORMATION: Synthetic - Primer

<400> SEQUENCE: 67
cttagcttgc ttgtcgaatg ggatatatgt ctttccg                           37

<210> SEQ ID NO 68
<211> LENGTH: 31
<212> TYPE: DNA
<213> ORGANISM: Artificial Sequence
<220> FEATURE:
<223> OTHER INFORMATION: Synthetic - Primer

<400> SEQUENCE: 68
atcccattcg acaagcaagc taaggagact g                                 31

<210> SEQ ID NO 69
<211> LENGTH: 54
<212> TYPE: DNA
<213> ORGANISM: Homo sapiens

<400> SEQUENCE: 69
atgaagtggg ttacctttat ctctttgttg tttcttttct cttctgctta ctct        54

<210> SEQ ID NO 70
<211> LENGTH: 18
<212> TYPE: PRT
<213> ORGANISM: Homo sapiens

<400> SEQUENCE: 70

Met Lys Trp Val Thr Phe Ile Ser Leu Leu Phe Leu Phe Ser Ser Ala
1               5                   10                  15

Tyr Ser

<210> SEQ ID NO 71
<211> LENGTH: 78
<212> TYPE: DNA
<213> ORGANISM: Saccharomyces cerevisiae

<400> SEQUENCE: 71
atgactaagc aacccaagt attagttaga tccgtcagta tattattttt catcacatta   60
ctacatctag tcgtagct                                                78
```

<210> SEQ ID NO 72
<211> LENGTH: 26
<212> TYPE: PRT
<213> ORGANISM: Saccharomyces cerevisiae

<400> SEQUENCE: 72

Met Thr Lys Pro Thr Gln Val Leu Val Arg Ser Val Ser Ile Leu Phe
1               5                   10                  15

Phe Ile Thr Leu Leu His Leu Val Val Ala
            20                  25

<210> SEQ ID NO 73
<211> LENGTH: 38
<212> TYPE: DNA
<213> ORGANISM: Artificial Sequence
<220> FEATURE:
<223> OTHER INFORMATION: Synthetic - Primer

<400> SEQUENCE: 73
gcgcctaggc cgcggcgaaa cgatgaagtg ggttacct                          38

<210> SEQ ID NO 74
<211> LENGTH: 37
<212> TYPE: DNA
<213> ORGANISM: Artificial Sequence
<220> FEATURE:
<223> OTHER INFORMATION: Synthetic - Primer

<400> SEQUENCE: 74
cgatgaagtg ggttaccttt atctctttgt tgtttct                           37

<210> SEQ ID NO 75
<211> LENGTH: 37
<212> TYPE: DNA
<213> ORGANISM: Artificial Sequence
<220> FEATURE:
<223> OTHER INFORMATION: Synthetic - Primer

<400> SEQUENCE: 75
ttatctcttt gttgtttctt ttctcttctg cttactc                           37

<210> SEQ ID NO 76
<211> LENGTH: 37
<212> TYPE: DNA
<213> ORGANISM: Artificial Sequence
<220> FEATURE:
<223> OTHER INFORMATION: Synthetic - Primer

<400> SEQUENCE: 76
tttctcttct gcttactctg ctccagtcaa cactaca                           37

<210> SEQ ID NO 77
<211> LENGTH: 38
<212> TYPE: DNA
<213> ORGANISM: Artificial Sequence
<220> FEATURE:
<223> OTHER INFORMATION: Synthetic - Primer

<400> SEQUENCE: 77
gcgcctaggc cgcggcgaaa cgatgactaa gccaaccc                          38

<210> SEQ ID NO 78
<211> LENGTH: 38
<212> TYPE: DNA
<213> ORGANISM: Artificial Sequence

```
<220> FEATURE:
<223> OTHER INFORMATION: Synthetic - Primer

<400> SEQUENCE: 78
cgatgactaa gccaacccaa gtattagtta gatccgtc                              38

<210> SEQ ID NO 79
<211> LENGTH: 38
<212> TYPE: DNA
<213> ORGANISM: Artificial Sequence
<220> FEATURE:
<223> OTHER INFORMATION: Synthetic - Primer

<400> SEQUENCE: 79
gtattagtta gatccgtcag tatattattt ttcatcac                              38

<210> SEQ ID NO 80
<211> LENGTH: 38
<212> TYPE: DNA
<213> ORGANISM: Artificial Sequence
<220> FEATURE:
<223> OTHER INFORMATION: Synthetic - Primer

<400> SEQUENCE: 80
tatattattt ttcatcacat tactacatct agtcgtag                              38

<210> SEQ ID NO 81
<211> LENGTH: 38
<212> TYPE: DNA
<213> ORGANISM: Artificial Sequence
<220> FEATURE:
<223> OTHER INFORMATION: Synthetic - Primer

<400> SEQUENCE: 81
tactacatct agtcgtagct gctccagtca acactaca                              38

<210> SEQ ID NO 82
<211> LENGTH: 29
<212> TYPE: DNA
<213> ORGANISM: Artificial Sequence
<220> FEATURE:
<223> OTHER INFORMATION: Synthetic - Primer

<400> SEQUENCE: 82
ctgaagcttg gtcagctgag gacaagcat                                        29

<210> SEQ ID NO 83
<211> LENGTH: 38
<212> TYPE: DNA
<213> ORGANISM: Artificial Sequence
<220> FEATURE:
<223> OTHER INFORMATION: Synthetic - Primer

<400> SEQUENCE: 83
ccggaattct tacctgtcac cgtaagtgtc gaaccata                              38
```

EFFICIENT PHOSPHOLIPASE C MUTANT THAT DOES NOT RELY ON ZINC IONS

CROSS-REFERENCE TO RELATED APPLICATIONS

This application represents the U.S. national stage entry of International Application No. PCT/CN2016/110030 filed Dec. 15, 2016, which claims priority to Chinese Patent Application No. 201510946696.1 filed Dec. 16, 2015, the disclosure of which is incorporated herein by reference in its entirety and for all purposes.

TECHNICAL FIELD

The invention relates to a zinc ion independent efficient phospholipase C mutant, particularly to a phosphatidylcholine specific phospholipase C mutant obtained by the mutant screening methods in molecular biology, and the use thereof.

BACKGROUND

Degumming is an important step in oil refining, and the traditional hydration degumming suffers from high cost, large material consumption and serious environmental pollution, therefore, many have been committed to using enzymatic degumming in the degumming procedure for oil refining and great progress has been made in recent years. Compared with traditional methods, enzymatic degumming can improve economic efficiency, save energy, reduce emission, decrease environment pollution, and have larger advantages in terms of environment, economic and quality. The enzyme used in oil degumming is phospholipase. Phospholipases possess the ability to hydrolyze one or more ester bonds of phosphoglyceride and represent a class of lipases, acyl hydrolases and phosphatases. Phospholipases, depending on its site of action in the phospholipid molecule, can be divided into phospholipase A1 (PLA1), phospholipase A2 (PLA2), phospholipase C (PLC) and phospholipase D (PLD).

Phospholipase C (for short, PLC), is a lipid hydrolase capable of hydrolyzing C3 phosphatidyl site of glycerophospholipids to form diacylglycerol and phosphorylcholine, inositol phosphates, phosphoethanolamine and other. Phospholipase C is widely found in plants and microorganisms. Plant and animal derived PLCs generally locate on cell membrane, which are complicated in structure, belonging to endogenous phospholipase C, and difficult to separate. Compared to other degumming enzymes, phospholipase C (PLC) showed greater advantages, such as increased yield of diacylglycerol (DAG), and reduced lose of obtained oil.

Microbial derived PLCs generally have simpler structures, and these enzymes have been isolated from various microorganisms, including many bacterial origin comprising *Clostridium perfringens* [Yun T, Siebel C. Cloning and expression of the PLC gene from *Clostridium perfringens* and *Clostridium bifermentants*[J]. Infection and immunity, 1989, 2: 468-476], *C. bifermentans, Burkholderia pseudomallei, Bacillus cereus, Bacillus mycoiddes, Bacillus thuringiensis, Listeria monocytogenes, Pseudomonas aeruginosa, P. fluorescens, Straphylococus aureus, Acinetobacter baumannii, Streptomyces clavuligerus, Burkholderi,* and others. They may be from actinomycetes such as *Streptomyces hachijyoensis,* and others. They may also be from yeasts such as *Candia albicans* [Analuz E, Juan-Jose R, Rosario Cueva. Sequencing of a 4.3 kbp region of chromosome 2 of *Candida albicans* reveals the presence of homologues of SHE9 from *Saccharomyces cerevisiae* and of bacterial phosphatidylinostiol-phospholipase C[J]. Yeast, 2001, 18(8): 711-721], *Saccharomyces cerevisiae* [Payne W, Fitzgerald-Hayes M. A mutation in PLC1, a candidate phosphoinositide specific phospholipase C gene from *Saccharomyces cerevisiae*, causes aberrant mitotic chromosome segregation[J]. Molecular and Cellular Biology, 1993, 13: 4351-4364], and others.

PC-PLC from *Bacillus cereus* (BC-PC-PLC) is an earlier studied phospholipase C. BC-PC-PLC has a full length of 283 amino acids, comprising a signal peptide of 24 amino acids and a leader peptide of 14 amino acids. The mature form thereof has 245 amino acids (Johansen, T., Holm, T., Guddal, P. H., Sletten, K., Haugli, F. B., Little, C, 1988, "Cloning and sequencing of the gene encoding the phosphatidylcholine-preferring phospholipase C of *Bacillus cereus*", Gene 65(2): 293-304). The crystal structure of BC-PC-PLC has been reported, which consists of a plurality of helical domains and has a catalytic site of aspartic acid 55 and at least three $Zn^{2+}$ binding sites (Hough., E., Hansen, L. K., Birknes, B., Jynge, K., Hansen, S., Hordvik, A., Little, C., Dodson, E., Derewenda, Z., 1989, "High-resolution (1.5 A) crystal structure of phospholipase C from *Bacillus cereus*", Nature, 338:357-60). Little has been studied about the heterologous expression of BC-PC-PLC other than that in *Bacillus subtilis* and *pichia pastoris* (Durban, M. A., Silbersack, J., Schweder, T., Schauer, F., Bornscheuer, U. T., 2007, High level expression of a recombinant phospholipase C from *Bacillus cereus* in *Bacillus subtilis*, Appl Microbiol Biotechnol 74(3):634-639; Seo, K. H, Rhee J. I., 2004, High-level expression of recombinant phospholipase C from *Bacillus cereus* in *Pichia pastoris* and its characterization, Biotechnol Lett 26(19):1475-1479).

Currently, phospholipase C is mainly used in enzymatic degumming. In the manufacture of edible oil such as soybean oil and rapeseed oil, unrefined crude oil mainly comprises a complex mixture of triglycerides, phospholipids, sterols, tocopherols, free fatty acids, trace metals and other trace compounds, wherein the phospholipid will cause deterioration of color and taste, shorter shelf life and affect the effect of subsequent refining process. Currently, the main degumming processes comprise hydration degumming, deep degumming and enzymatic degumming. Enzymatic degumming is becoming preferred due to its mild condition, non-pollution, and low oil consumption.

Since phospholipase C can act on glycerophospholipids to generate diacylglycerol, use of phospholipase C in the enzymatic degumming process thus can significantly improve the yield of oil, thereby enhancing the economic efficiency of production. Therefore, it is of important practical significance to improve the degumming performance of phospholipase C.

However, there is still need of BC-PC-PLC with a higher enzymatic activity in the field.

SUMMARY

In the invention, asparagines in three glycosylation sites of BC-PC-PLC, i.e., positions 63, 131 and 134 are mutated to aspartic acid, serine, and aspartic acid, respectively (see SEQ ID NO: 2), which increase the enzymatic activity by 16-fold in the presence of low zinc sulfate compared to the wild-type enzyme.

Further, in the invention, error-prone PCR is used to provide a mutant library of SEQ ID NO: 2, the expression vector within the mutant library is transformed to *Pichia* host cell to obtain several mutant strains with a specific activity (U/mg of total protein) similar to or 1.5 times higher than the parent (i.e., SEQ ID NO: 2 amino acid sequence shown) by plate screening, tyrosine at position 56 of the amino acid sequences of these mutants is mutated to alanine (A), lysine (K), asparagine (N), glutamine (Q), histidine (H), tryptophan (W), phenylalanine (F), arginine acid (R), serine (S) or threonine (T). In particularly, the mutants with W or H at position 56 have a specific activity 7 times higher than the parent.

The invention therefore provides a zinc ion independent efficient phospholipase C mutant, which can be used in various aspects such as oil refining, phospholipid modification, feed modifier, food industry and pharmaceutical industry, and others, thereby completing the invention.

Accordingly, a first aspect of the invention provides an isolated amino acid sequence comprising:

(1) an amino acid sequence as set forth in SEQ ID NO: 7; or (2) a polypeptide derived from the amino acid of (1) by substitution, deletion or addition of one or several amino acids in the amino acid sequence in (1) while retaining the phospholipase C activity of SEQ ID NO: 7.

In one or more embodiments, the amino acid Xaa at position 56 of SEQ ID NO: 7 is alanine, lysine, asparagine, glutamine, histidine, or tryptophan.

In one or more embodiments, the amino acid Xaa at position 56 of SEQ ID NO: 7 is histidine or tryptophan.

In one or more embodiments, the substitution, deletion or addition of one or more amino acids in (2) is M to V mutation at position 106.

In one or more embodiments, the substitution, deletion or addition of one or more amino acids in (2) is R to H mutation at position 20.

In one or more embodiments, the substitution, deletion or addition of one or more amino acids in (2) is A to D mutation at position 83.

In one or more embodiments, the amino acid residual at position 56 of the amino acid sequence in (2) is histidine, and that at position 106 is valine.

In one or more embodiments, the amino acid sequence comprises a signal peptide (e.g., leader peptide), terminal extension, GST, maltose E binding protein, protein A, tag (such as a 6His or Flag), and/or protease hydrolysis sites for factor Xa or thrombin or enterokinase, or consists of one or more of these sequences and the amino acid sequence as set forth in SEQ ID NO: 7.

In one or more embodiments, the amino acid sequence of the signal peptide is set forth in SEQ ID NO: 70 or 72.

In one or more embodiments, the amino acid sequence is selected from SEQ ID NOs: 2, 4 and 6.

A second aspect of the invention provides an isolated polynucleotide sequence selected from:

(1) a polynucleotide sequence encoding an isolated polypeptide according to the invention;

(2) a complementary sequence to the polynucleotide of (1); and (3) a fragment of the sequence of (1) or (2) with 15-30 bases.

In one or more embodiments, the polynucleotide sequence is set forth in SEQ ID NO: 1, 3 or 5.

A third aspect of the invention provides a nucleic acid construct, wherein the nucleic acid construct comprises a polynucleotide sequence according to the invention.

In one or more embodiments, the nucleic acid construct is an expression vector or cloning vector.

The invention further provides a genetically engineered host cell, the host cell:

(1) expresses the amino acid sequence according to the invention; and/or (2) comprises a polynucleotide sequence or nucleic acid construct according to the invention.

The invention also provides a composition comprising a polypeptide according to the invention and optionally auxiliary materials, preferably, the auxiliary materials are absorbing materials selected from activated carbon, alumina, diatomaceous earth, porous ceramics, and porous glass.

The invention also provides use of an amino acid sequence according to the invention in oil refining, phospholipid modification, feed modifier, food industry and pharmaceutical industry.

The invention also provides a method for enzymatic degumming, the method comprises incubating phospholipase C at a temperature between 55° C. and 75° C., adding phospholipase C to the crude oil for degumming.

In one or more embodiments, the phospholipase C have the amino acid sequence according to the invention.

In one or more embodiments, phospholipase C, especially the amino acid sequence according to the invention is incubated at a temperature between 60° C. and 70° C.

In one or more embodiments, the incubation time is between 15 and 45 minutes.

In one or more embodiments, based on the weight of crude oil, the enzyme is added in an amount of 50 to 1000 ppm, preferably 100 to 500 ppm, more preferably 100 to 300 ppm.

In one or more embodiments, the enzyme is incubated in an aqueous solution.

In one or more embodiments, prior to adding the enzyme to crude oil, the crude oil is first heated to 50 to 70° C., preferably 50 to 60° C.

In one or more embodiments, degumming comprises stirring at 50 to 60° C. for 1 to 3 hours, and then raising the temperature to 80 to 90° C. and then holding for 1 to 10 minutes.

The invention also provides a method for improving degumming performance of phospholipase C, the method comprises incubating phospholipase C at a temperature between 55° C. and 75° C., adding phospholipase C to crude oil for degumming.

In one or more embodiments, the phospholipase C has the amino acid sequence according to the invention.

In one or more embodiments, phospholipase C, especially the amino acid sequence according to the invention is incubated at a temperature between 60° C. and 70° C.

In one or more embodiments, the incubation time is between 15 and 45 minutes.

In one or more embodiments, based on the weight of crude oil, the enzyme is added in an amount of 50 to 1000 ppm, preferably 100 to 500 ppm, more preferably 100 to 300 ppm.

In one or more embodiments, the enzyme is incubated in an aqueous solution.

In one or more embodiments, prior to adding the enzyme to crude oil, the crude oil is first heated to 50 to 70° C., preferably 50 to 60° C.

In one or more embodiments, degumming comprises stirring at 50 to 60° C. for 1 to 3 hours, and then raising the temperature to 80 to 90° C. and holding for 1 to 10 minutes.

In one or more embodiments, the crude oil comprises but not limited to soybean oil, sunflower oil, peanut oil, rapeseed oil, rice bran oil, corn oil, olive oil, palm oil, palm kernel oil, palm soft fat, canola oil, castor oil, coconut oil, coriander oil, cottonseed oil, hazelnut oil, hempseed oil, linseed oil, mango kernel oil, meadowfoam oil, neat's foot oil, safflower oil, *camellia* oil, tall oil, *camellia* oil and other vegetable oils.

EMBODIMENT

Polypeptides Having the Phospholipase C Activity

Figure 1:
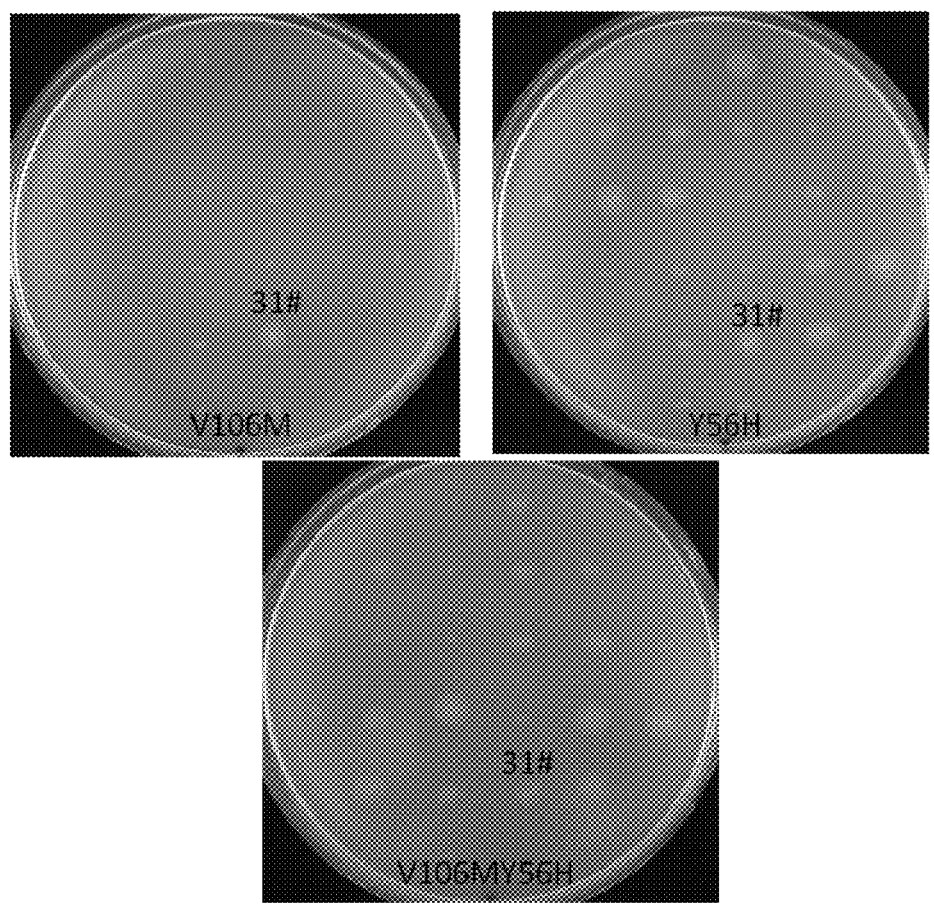
FIG. 1 shows the results of culturing three mutants PLC-N63DN131SN134D-Y56H, PLC-N63DN131SN134D-M106V and PLC-N63DN131SN134D-Y56HM106V in BMM-soybean phospholipids screening plates with 10 µM ZnSO$_4$.

The invention provides a polypeptide having the amino acid sequence as set forth in SEQ ID NO: 7. The invention further comprises a polypeptide comprising one or more (typically 1-10, e.g. 8, 9, or 10) amino acid deletions, insertions and/or substitution based on SEQ ID NO: 7, in particular addition of one or more (typically 20 or less, preferably 10 or less, more preferably 8 or less) amino acids at C-terminus and/or N-terminus. These variant forms still have the phospholipase C activity according to the invention. As an example of such mutation, the invention comprises phospholipase C of SEQ ID NO: 7 with a mutation of R to H at position 20, a mutation of A to D at position 83 and/or a mutation of M to V at position 106.

Conservative variant forms are preferred. For example, in the art, when conservative substitution of amino acids with close or similar properties is performed, the function of the protein or polypeptide typically does not change. "Amino acids with close or similar properties" includes, for example, a family of amino acid residues having similar side chains. Such family includes amino acids having basic side chain (e.g., lysine, arginine, histidine), amino acids having acidic side chain (e.g. aspartic acid, glutamic acid), amino acids having uncharged polar side chain (e.g. glycine, asparagine, glutamine, serine, threonine, tyrosine, cysteine acid), amino acids having nonpolar side chain (e.g., alanine, valine, leucine, isoleucine, proline, phenylalanine, methionine, tryptophan), amino acid having (3-branched side chains (e.g., threonine, valine, isoleucine) and amino acid having aromatic side chain (e.g., tyrosine, phenylalanine, tryptophan, histidine). Thus, in the polypeptide according to the invention, replacement of one amino acid residue from a class of same side chain with another at one or more positions will not substantially affect its activity.

Furthermore, as well known to those skilled, in the cloning operation, it is often required to design suitable enzymatic cleaving sites, which would introduce one or more irrelevant residues at the terminus of the protein expressed without affecting the activity of the protein of interest. In another example, in order to construct fusion protein, facilitate expression of a recombinant protein, obtain recombinant protein that auto-secrete to outside of a host cell, or facilitate purification of recombinant proteins, it is often necessary to add some amino acids to the N-terminus, C-terminus of the recombinant protein or the other suitable region within the said protein, e.g., including but not limited to, a suitable linker peptide, signal peptide, leader peptide, terminal extension, glutathione S-transferase (GST), maltose E binding protein, protein A, tag such as 6His or Flag, or protease hydrolysis sites for factor Xa or thrombin or enterokinase. It should be understood that the presence of these amino acid sequences does not affect the activity of the resulted polypeptide. Accordingly, the invention also comprises addition of one or more amino acids at the C-terminus and/or N-terminus of the polypeptide according to the invention (e.g., the previous linker peptide, signal peptide, leader peptide terminal extension, GST, maltose E binding protein, protein A, tag such as 6His tag or Flag, or protease hydrolysis sites for factor Xa or thrombin or enterokinase, etc.) of the resultant polypeptide, wherein such polypeptide still has the phospholipase C activity described herein. In certain embodiments, the invention uses α-mating factor signal sequence from *Saccharomyces cerevisiae*, serum albumin signal sequence from *Homo sapiens* and killer protein signal sequence from *Saccharomyces cerevisiae*. In certain embodiments, the coding sequence and amino acid sequence of the albumin signal peptide are set forth as SEQ ID NOs: 69 and 70, respectively. In certain embodiments, the coding sequence and amino acid sequence of the killer protein signal sequence from *Saccharomyces cerevisiae* are set forth as SEQ ID NOs: 71 and 72, respectively. In certain embodiments, the amino acid sequence of the α-mating factor signal sequence from *Saccharomyces cerevisiae* is an amino acid sequence encoded by position 8-64 of SEQ ID NO: 10.

In certain aspects, the invention provides a polypeptide sequence having at least 80%, at least 85%, at least 90%, at least 95%, at least 97% or at least 99% sequence identity to SEQ ID NO: 7, and its phospholipase activity is comparative or superior to the polypeptide as set forth in SEQ ID NO: 7 (particularly SEQ ID NOs: 2, 4 or 6). The sequence identity of two sequences may be aligned with conventional methods in the art, for example, Protein BLAST from NCBI.

Based on the host used in the recombinant production protocol, the polypeptide according to the invention may be glycosylated, or may be non-glycosylated.

The polypeptide according to the invention may be a naturally purified product, or a chemically synthesized product, or produced from a prokaryotic or eukaryotic host (e.g., bacterial, yeast, higher plant, insect and mammalian cells) using recombinant techniques.

Polynucleotide

The application comprises a nucleotide sequence encoding a polypeptide according to the invention or its complementary sequence. Examples of the coding sequence of a polypeptide according to the invention are set forth in SEQ ID NOs: 1, 3 and 5. The "coding sequence" comprises a nucleic acid sequences encoding the polypeptide according to the invention (in particular, SEQ ID NO: 7). The sequence encoding a polypeptide according to the invention may be identical to, for example, the coding regions as set forth in SEQ ID NOs: 1, 3 and 5, or may be its degenerate variant. As used herein, "degenerate variant" means the case wherein the amino acid sequences are same, but the nucleotide sequences are different.

The sequence encoding a polypeptide according to the invention comprises: the coding sequence encoding only the mature polypeptide; the coding sequence for the mature polypeptide and various additional coding sequences; and the coding sequence for the mature polypeptide (and optionally an additional coding sequence) and a non-coding sequence.

The invention further relates to a variant of the polynucleotide described above, which encodes fragment, analog, derivative and variant forms of the same amino acid sequence according to the invention. Such variant of the polynucleotide may be a naturally occurring allelic variant or a non-naturally occurring variant. These nucleotide variants comprise substitution variants, deletion variants, and insertion variants. As known in the art, an allelic variant is an alternate form of a polynucleotide, which may be one or more nucleotide substitutions, deletions or insertions, but would not substantially alter function of the protein to be encoded.

The invention also comprises a fragment of a nucleic acid sequence encoding a polypeptide according to the invention (e.g., SEQ ID NOs: 1, 3, 5, or its complementary sequence). As used herein, a "nucleic acid fragment" has at least 15 nucleotides, preferably at least 30 nucleotides, more preferably at least 50 nucleotides, most preferably at least 100 nucleotides or more in length. A nucleic acid fragment may be used in nucleic acid amplification techniques (e.g. PCR) to identify and/or separate a polynucleotide encoding a polypeptide according to the invention. Thus, in some embodiments, the nucleic acid fragment has 15-30 bases in length. An appropriate nucleic acid fragment may be selected from a nucleic acid sequence according to the invention using the prior art as a primer or probe.

A coding sequence of a polypeptide according to the invention or its fragment can be obtained by PCR amplification, recombination or synthetic methods. For PCR amplification, primers may be designed based on a related nucleotide sequence disclosed in the invention, in particular open reading frame sequence, and a commercially available cDNA library or a cDNA library prepared using conventional methods known in the art is used as a template for amplifying and obtaining the related sequence. When the sequence is long, it is often required to conduct two or more PCR amplifications, and then ligating the amplified fragments from each time together in a correct order.

Nucleic Acid Construct

The invention also relates to a nucleic acid construct comprising an isolated polypeptide according to the invention operably linked to one or more regulatory sequences that are expressed in a suitable host cell under appropriate conditions for the regulatory sequences. Polynucleotide encoding a polypeptide according to the invention may be operated in various ways to ensure the expression of the polypeptide. Prior to its insertion into a vector, the operation of a polynucleotide sequence may be desirable or necessary for the expression vector. Methods for utilizing recombinant DNA techniques to alter a polynucleotide sequence are known in the art.

The regulatory sequence may be a suitable promoter sequence for expressing a nucleotide sequence recognized by a host cell for expression of a polynucleotide encoding a polypeptide according to the invention. The promoter sequence comprises transcriptional regulatory sequences linked to the polypeptide to be expressed. The promoter may be any nucleotide sequence that exhibits transcriptional activity in the selected host cell, including mutant, truncated, and hybrid promoters, and can be obtained from genes encoding extracellular or intracellular polypeptides homologous or heterologous to the host cell.

Examples of a suitable promoter that directs nucleic acid constructs according to the invention to transcribe especially in a bacterial host cell is a promoter obtained from bacteriophage T7, *E. coli* lac operon, *Streptomyces coelicolor* agarase gene, *Bacillus subtilis* levansucrase gene, *Bacillus licheniformis* α-amylase gene, *Bacillus amyloliquefaciens* α-amylase gene, *Bacillus licheniformis* penicillinase genes.

Examples of a suitable promoter that directs the nucleic acid construct according to the invention to positively transcribe in a filamentous fungal host cell is a promoter obtained from *Aspergillus oryzae* TAKA amylase, *Rhizomucor miehei* aspartic proteinase, *Aspergillus niger* neutral α-amylase, *A. niger* acid stable α-amylase, *Aspergillus niger* or *Aspergillus awamori* glucoamylase (glaA), *Trichoderma reesei* cellobiohydrolase enzymes I, *Trichoderma reesei* cellobiohydrolase II enzymes, *Aspergillus oryzae* alkaline protease, *Aspergillus oryzae* triose phosphate isomerase, *Trichoderma reesei* glucanase gene or its mutant, truncated, and hybrid promoter.

In yeast host, useful promoter may be obtained from *Saccharomyces cerevisiae* enolase (ENO-1), *Saccharomyces cerevisiae* galactokinase (GAL1), *Saccharomyces cerevisiae* alcohol dehydrogenase, glyceraldehyde-3-phosphate dehydrogenase, *Saccharomyces cerevisiae* triosephosphate isomerase, *Saccharomyces cerevisiae* 3-phosphoglycerate kinase gene, *Pichia pastoris* alcohol oxidase gene. Other useful promoters for yeast host cells are described in Romanos et al., 1992, Yeast 8: 423-488.

The regulatory sequence may also be a suitable transcription terminator sequence, a sequence recognized by a host cell terminate transcription. A terminator sequence is operably linked to the 3' end of a nucleotide sequence encoding the polypeptide. Any terminator that is functional in the selected host cell can be used in the invention.

A preferred terminator for bacterial host may be a terminator derived from the bacteriophage T7.

A preferred terminator for filamentous fungal host cells is obtained from *Aspergillus oryzae* TAKA amylase, *Aspergillus niger* glucoamylase, *Aspergillus nidulans* anthranilate synthase, *Aspergillus niger* α-glucosidase.

A preferred terminator for a yeast host cell is obtained from *Saccharomyces cerevisiae* enolase, *Saccharomyces cerevisiae* cytochrome C, *Saccharomyces cerevisiae* glyceraldehyde-3-phosphate dehydrogenase, *Pichia pastoris* alcohol oxidase genes.

The regulatory sequence may also be a suitable leader sequence, a non-translated region of the mRNA important for the translation of the host cell. The leader sequence is operably linked to 5' end of a nucleotide sequence encoding the polypeptide. Any leader sequence that is functional in the selected host cell may be used in the invention.

The regulatory sequence may also be a signal peptide coding region that encodes an amino acid sequence linked to the amino-terminal of a polypeptide and directs the encoded polypeptide into the signal peptide coding region in the cell secretory pathway. 5' end of the coding sequence of the nucleotide sequence may inherently contain a signal peptide coding region naturally linked to translation reading frame comprising the coding section that encodes the secreted polypeptide. Alternatively, the 5' end of the coding sequence may contain a signal peptide coding region which is foreign to the coding region. When the coding sequence does not naturally contain a signal peptide coding region, a foreign signal peptide coding region may be required. Alternatively, the foreign signal peptide coding region may simply replace the natural signal peptide coding region to enhance secretion of the polypeptide. However, any signal peptide coding region that directs the expressed polypeptide to enter the secretory pathway in the selected host cell of choice can be used in the invention. In certain embodiments, the invention uses α-mating factor signal sequence, albumin signal sequence from *Homo sapiens* and killer protein signal sequence from *Saccharomyces cerevisiae*. In certain embodiments, the coding sequence and amino acid sequence of albumin signal sequence are set forth in SEQ ID NOs: 69 and 70, respectively. In certain embodiments, the coding sequence and amino acid sequence of the killer protein signal sequence from *Saccharomyces cerevisiae* are set forth as SEQ ID NOs: 71 and 72, respectively. In certain embodiments, the coding sequence of the α-mating factor signal sequence is set forth as positions 8-64 of SEQ ID NO: 10.

Vector

The invention also relates to a vector comprising a polynucleotide according to the invention, including but not limited to a cloning vector and an expression vector. For example, in certain embodiments, the nucleic acid constructs according to the invention is an expression vector or a cloning vector.

In the expression vector, various nucleic acid and regulatory sequences may be linked together to produce a recombinant expression vector that may include one or more convenient restriction sites for insertion or substitution of a polynucleotide sequence that encodes the polypeptide at such sites. Alternatively, a nucleotide sequence according to the invention can be expressed by a nucleic acid construct with nucleotide sequence inserted or comprising a sequence within a suitable expression vector. In the constructiion of an expression vector, a coding sequence is located in the vector so that the coding sequence is operably linked for appropriate expression of a regulatory sequence.

The recombinant expression vector may be any vector (e.g., a plasmid or virus) that is conveniently subjected to a recombinant DNA method and can result in the expression of a nucleotide sequence of interest. The selection of vector depends on the compatibility of the vector and the host cell into which the vector is introduced. The vector may be a linear or closed circular plasmid.

The vector may be an autonomously replicating vector, which exists as an extrachromosomal entity and its replication does not rely on chromosomal replication, e.g., a plasmid, an extrachromosomal element, minichromosome or an artificial chromosome. The vector may contain any means for assuring self-replication. Alternatively, the vector may be a vector that when introduced into a host cell, it integrates into the genome and replicates with the vector chromosome into which it has integrated. Furthermore, a single vector or plasmid, or two or more vectors or plasmids, or a transposon together comprising total DNA to be introduced into the host cell genome can be used.

A preferred vector according to the invention comprises one or more selectable markers that permit easy selection of transformed, transfected, transduced cells and the like. A selectable marker is a gene whose product provides resistance to antibiotics or viruses, resistance to heavy metals, prototrophy to auxotrophs and the like.

A preferred vector according to the invention comprises an element that allows integration of the vector into the host cell genome or autonomous replication of the vector independent from the genome.

More than one copy of the polynucleotide according to the invention can be inserted into the host cell to increase production of the gene product. Increasing the copy number of the polynucleotide can be achieved by integrating at least one additional copy of the sequence into the host cell genome or by including an amplifiable marker gene and the polynucleotide containing an amplified copy of the selectable marker gene, thereby a cell comprising an additional copy of a polynucleotide may be screened by culturing in the presence of a suitable selective agent.

A preferred vector according to the invention comprises an artificially synthesized sequence containing several restriction enzyme recognition sites, which can provide a variety of positions to be inserted or insertion strategy for exogenous DNA.

The expression vector according to the invention may be more preferably selected as a vector for expression in *Pichia*. The vector according to the invention is preferably a commercially available vector for use in *Pichia*, such as a series of vectors, pPIC, pPICZ, pAO, pGAP, pGAPZ or the like.

A cloning vector comprising a polynucleotide according to the invention may be used to replicate a sufficient number of target plasmid. Accordingly, the cloning vector according to the invention has a stronger self-replicating element, such as an origin of replication and the like. Typically, the cloning vector according to the invention does not have an expression element.

Host Cell

The invention also relates to a recombinant host cell comprising a polynucleotide according to the invention for recombinantly producing a polypeptide. A vector comprising a polynucleotide according to the invention is introduced into a host cell so that the vector is maintained as a part of the chromosome or as an extrachromosomal self-replicating vector as described earlier. The selection of a host cell largely depends on the polypeptide encoding gene and its source.

The host cell may be a unicellular microorganism or a non-unicellular microorganism. Unicellular microorganisms such as gram positive bacteria include but not limited to, a *Bacillus* cell, e.g., *Bacillus alkalophilus, Bacillus amyloliquefaciens, Bacillus brevis, Bacillus megaterium, Bacillus subtilis, Bacillus licheniformis, Bacillus coagulans, Bacillus stearothermophilus, Bacillus thuringiensis* and the like; or a *Streptomyces* cell, e.g., *Streptomyces lividans*; or gram negative bacteria such as *E. coli* and *Pseudomonas* sp. In a preferred aspect, the bacterial host is *Bacillus subtilis, E. coli, Bacillus licheniformis, Bacillus stearothermophilus* and *E. coli* cells.

The host cell may be a eukaryote, such as a mammalian, insect, plant, yeast or fungal cell. In a preferred aspect, the host cell is a eukaryotic cell, as used herein, "eukaryotic" includes the Ascomycota, Basidiomycota, Chytridiomycota, Zygomycota, Oomycota and the like.

In a more preferred aspect, the host cell is a cell of Ascomycota such as *Saccharomyces, Pichia, Yarrowia, Candida* and *Komagataella*.

In a most preferred aspect, the host cell is *Pichia pastoris, Saccharomyces cerevisiae, Yarrowia lipolytica* and the like. In another most preferred aspect, the host cell is a *Pichia pastoris* cell.

Production Method

After obtaining the coding sequence of a polypeptide, a method may be employed for producing a polypeptide according to the invention, the method comprising: (a) culturing a host cell containing an expression vector of the polypeptide under conditions conducive to production of the polypeptide; and (b) recovering the polypeptide.

In production method according to the invention, the cells may be cultured in a medium suitable for the production of the polypeptide using methods known in the art. For example, the cells can be subjected to the shake flask culture in laboratory or industrial fermentors and small-scale or large-scale fermentation (including continuous, batch, feed-batch, or solid state fermentations), and cultured in a suitable medium and conditions allowing expression and/or separation of the polypeptide. The cultivation takes place in a suitable media comprising carbon and nitrogen sources and inorganic salts using methods known in the art. A suitable media may be obtained from a commercial supplier or may be prepared according to a published composition. If the polypeptide is secreted into the medium, the polypeptide can be recovered directly from the medium. If the polypeptide is not secreted into the medium, it can be recovered from cell lysates.

In certain embodiments, as previously described, the invention preferably constructs an expression vector of phospholipase C with serum albumin signal sequence from *Homo sapiens* or the killer protein signal sequence from *Saccharomyces cerevisiae* as the signal peptide. After introduced into an expressing strain, the stain is cultured under conditions conducive to production of phospholipase C and the phospholipase C is recovered. In certain embodiments, the strain is *Pichia pastoris*. The method for cultivation or fermentation of said strain may be a conventional fermentation method in the art.

Alternatively, a polypeptide according to the invention may also be synthesized with a chemical synthesis method known in the art. Chemical synthesis methods for a polypeptide include solid-phase synthesis and liquid phase synthesis method, wherein the solid phase synthesis is commonly used. Solid phase synthesis methods include, but not limited to two common methods, Fmoc and tBoc. Typically, resin is used as an insoluble solid support, and amino acids are typically connected one by one from the C-terminus (carboxy terminus) to the N-terminus (amino terminus) onto the peptide chain, each amino acid linkage cycle consists of the following three steps: 1) deprotection: in a protected amino acid, the protecting group of the amino acid must be removed using a de-protecting solvent; 2) activation: the carboxyl group of the amino acid to be connected is activated by an activator; and 3) coupling: the activated carboxyl is reacted with the exposed amino group of the previous amino acid to form a peptide bond. The cycle is repeated until the peptide chain is extended to a desirable length. Finally, the connection between the solid support and the peptide chain is cleaved by cleaving solution, and the desired amino acid sequence can be obtained. Above chemical synthesis could be conducted on a program-controlled automated peptide synthesizer, such instruments include but not limited to Tribute dual-channel peptide synthesizer from Protein Technologies, UV Online Monitor System from CS Bio Company, Focus XC three channel synthesizer from Aapptec and the like.

The polypeptide described herein may be recovered with a known method according to the invention. For example, a polypeptide may be recycled from the media by conventional methods, including but not limited to, centrifugation, filtration, ultrafiltration, extraction, chromatography, spray drying, freeze drying, evaporation, precipitation or the like.

A polypeptide according to the invention can be purified by a variety of methods known in the art, including but not limited to, chromatography (e.g., ion exchange, affinity, hydrophobic, chromatofocusing, size exclusion), electrophoresis (e.g., isoelectric focusing), differential solubility (such as salting-out precipitation), SDS-PAGE, or extraction method to obtain a substantially pure polypeptide.

Properties and Uses of the Polypeptide

A polypeptide according to the invention has phospholipase C activity, which may be used for oil refining, phospholipid modification, feed modifier and various aspects in food industry and pharmaceutical industry, including but not limited to baking, detergents, improvement of filtration of aqueous or syrup and the like.

A polypeptide according to the invention may be provided in form of pure enzyme preparation, or in form of a composition. The composition may be a powdered composition, a liquid composition, or a pasty composition. When provided in the form of composition, the composition may contain various excipients according to the different uses of the enzyme-containing composition. Excipients known in the art may be added to the compositions according to the invention, and such excipients include but are not limited to, sorbitol, potassium sorbate, methyl benzoate, ethyl benzoate, sucrose, mannitol, trehalose, starch, sodium chloride, calcium chloride, other stabilizers or one or more other substances.

The amount of the polypeptide according to the invention used in the method according to the invention can be practically determined.

Enzymatic Degumming

The invention also provides a method for enzymatic degumming, the method comprises incubating phospholipase C at a temperature between 55° C. and 75° C., then adding phospholipase C to crude oil for degumming.

As described above, a polypeptide according to the invention may be used for the enzymatic degumming in oil and fat production. Accordingly, the invention provides a method of degumming, comprising adding a polypeptide according to the invention to crude oil for degumming.

A polypeptide according to the invention can be directly added to crude oil to be degummed, and then degumming under conventional degumming conditions. Alternatively, it is preferred that the polypeptide according to the invention is incubated at a temperature between 55° C. and 75° C., preferably at a temperature between 60° C. and 70° C., then added to the crude oil for degumming. The incubation time is usually 15 to 45 minutes, preferably 20 to 40 minutes.

Typically, the crude oil is heated to 50 to 70° C., preferably 50 to 60° C., and then added to an incubated or unincubated enzyme.

Enzymes are normally added as aqueous solution. Based on the weight of crude oil, the enzyme is added in an amount of 50 to 1000 ppm, preferably 100 to 500 ppm, more preferably 100 to 300 ppm.

Degumming conditions typically include: stirring at 50 to 60° C. for 1 to 3 hours, and then heating to 80 to 90° C. for 1 to 10 minutes.

Another aspect of the invention further provides a method for improving degumming performance of phospholipase C, the method comprises the steps of: incubating phospholipase C at a temperature between 55° C. and 75° C., preferably 60° C. to 70° C., and then adding it to crude oil for degumming. As previously described, the phospholipase C may be a polypeptide according to the invention. The incubation time is usually 15 to 45 minutes, preferably 20 to 40 minutes. Typically, the crude oil is first heated to 50° C. to 70° C., preferably 50° C. to 60° C., and then into which incubated or unincubated enzyme is added. The enzyme is normally added in an aqueous solution. Based on the weight of crude oil, the enzyme is added in an amount of 50 to 1000 ppm, preferably 100 to 500 ppm, more preferably 100 to 300 ppm.

Degumming conditions typically comprise: stirring at 50 to 60° C. for 1 to 3 hours, and then heating to 80 to 90° C. for 1 to 10 minutes.

Crude oil suitable for the degumming process of the invention include, but are not limited to soybean oil, sunflower oil, peanut oil, rapeseed oil, rice bran oil, corn oil, olive oil, palm oil, palm kernel oil, palm olein, canola oil, castor oil, coconut oil, coriander oil, cottonseed oil, hazelnut oil, hempseed oil, linseed oil, mango kernel oil, meadowfoam oil, neat's foot oil, safflower oil, *camellia* oil, tall oil, *camellia* oil and other vegetable oils.

The invention would be illustrated with specific examples hereinafter. Experimental methods with no specific conditions specified in the examples below, are performed under routine conditions, such as those in Sambrook et al., "Molecular Cloning: A Laboratory Manual" (New York: Cold Spring Harbor Laboratory Press (Cold Spring Harbor Laboratory Press), 1989), or the conditions recommended by the manufacturer. For usage and dosage of reagents, unless otherwise specified, they are used in accordance with conventional usage and dosage.

Experimental Materials

1. Experimental Strains and Plasmids

Strain: *Pichia* SMD1168 (Invitrogen, #C175-00), *E. coli* DH5a (TAKARA: Catalog #. D9057A).

Plasmid: pAO815 plasmid (Invitrogen, #V180-20), pAO-PLC plasmid (constructed by our laboratory), pmAO-PLC plasmid (constructed by our laboratory).

2. Mediums and Solutions

LB liquid medium: 0.5% yeast extract, 1% tryptone, 1% NaCl, pH7.0.

LB solid medium: LB liquid medium with agar at a concentration of 1.5%.

YPD liquid medium: 1% yeast extract, 2% peptone, 2% glucose.

YPD solid medium: LB liquid medium with agar at a concentration of 2%.

MGYS solid medium: 1.34% yeast nitrogen base (YNB) containing amino acid-free ammonium sulfate, 1% glycerol, 1M sorbitol, $4\times10^{-5}$% D-biotin, 2% agar.

BMM-soybean phospholipid selection medium: 1.34% yeast nitrogen base (YNB) containing amino acid-free ammonium sulphate, $4\times10^{-5}$% D-biotin, 0.5% methanol (added after sterilization), 2% soybean phospholipid emulsion solution, 0.1 M citric acid-sodium citrate buffer pH 6.6, 2% agar, with $ZnSO_4.7H_2O$ added.

2% soybean phospholipid emulsion: 2 g soybean phospholipid, 100 ml $H_2O$, homogenized at 8000 rpm using a high speed homogenizer for 1 min.

BMGY liquid medium: 1% yeast extract, 2% peptone, 1.34% yeast nitrogen base (YNB) containing ammonium sulfate without amino acids, 1% glycerol, $4\times10^{-5}$% D-biotin, 0.1M phosphate dihydrate potassium-dipotassium phosphate buffer pH6.0.

BMMY liquid medium: 1% yeast extract, 2% peptone, 1.34% yeast nitrogen base (YNB) containing amino acid-free ammonium sulfate, 0.3% $ZnSO_4.7H_2O$, 0.5% methanol (added after sterilization), $4\times10^{-5}$% D-biotin (added after sterilization), 0.1M citric acid-sodium citrate buffer at pH6.6.

Soybean phospholipid is purchased from Beijing Meryas Phospholipid Technology Co., FPLA grade Yeast extract and tryptone are purchased from OXOID, peptone and yeast nitrogen base purchased from BD, biotin is purchased from Shanghai Sangon, ammonium sulfate, citric acid, and sodium citrate are purchased from Sinopharm, analytical grade.

Chemicals not specified in the invention are all purchased from Sinopharm, analytical grade.

3. Reagents Used in Molybdenum Blue Assay for PLC Viability:

PLC reaction solution: 0.5% soybean phospholipid, 25 mM citric acid-sodium citrate buffer at pH 6.6, 10 uM $ZnSO_4$;

CIAP reaction solution: 50 mM Tris-HCl pH 9.0, 10 mM $MgCl_2$, 1 U CIAP (commercially available from TaKaRa Biotechnology (Dalian) Co., Ltd.);

Molybdenum blue development reaction solution: 100 ul CIAP reactant, 0.2% ascorbic acid, 0.1% ammonium molybdate (formulated with 30% $H_2SO_4$);

Modified Bradford protein concentration assay kit (purchased from Shanghai Sangon Biological Engineering Co., Ltd.);

Restriction enzyme HindIII, EcoRI (purchased from New England Biotechnology (Beijing) Ltd.);

PCR enzyme: TaKaRa Taq, PrimeSTAR® HS the DNA Polymerase (purchased from TaKaRa Biotechnology (Dalian) Co., Ltd.);

T4 DNA ligase (purchased from Fermentas).

4. The Primers Used are Listed in Table 1 Below:

TABLE 1

| Primer Name | Primer Sequence 5'-3' |
|---|---|
| AmPLC-1 | CCGGACGTCGCTAGCAGATCTAACATCCAAAGACG (SEQ ID NO: 11) |
| AmPLC-2 | TCATCGTTTCGCCTAGGATCCTTCGAATAATTAGTTG (SEQ ID NO: 12) |
| AmPLC-3 | GATCCTAGGCGAAACGATGAGATTTCCTTC (SEQ ID NO: 13) |
| AmPLC-4 | CCGGAATTCTTACCTGTCACCGTAAG (SEQ ID NO: 14) |
| AOXH-2 | GTTAAAATCAAAACGTTGTCAATTGGAACCAGTCG (SEQ ID NO: 15) |
| AOXH-3 | CCAATTGACAACGTTGATTTTAACGACTTTTAACGACAAC (SEQ ID NO: 16) |
| AOX1-5 | CGACTGGTTCCAATTGACAACG (SEQ ID NO: 17) |
| AOX1-3 | GGCAAATGGCATTCTGACATCCTC (SEQ ID NO: 18) |
| EPPLC-1 | CCCAAGCTTGGTCAGCTGAGGAC (SEQ ID NO: 19) |
| EPPLC-2 | CCGGAATTCTTACCTGTCACCGTA (SEQ ID NO: 20) |
| 63D-2 | CGAAGGTACTGTCATCGTAATAGGGGTTTTCATAATC (SEQ ID NO: 21) |

TABLE 1-continued

| Primer Name | Primer Sequence 5'-3' |
|---|---|
| 63D-3 | CTATTACGATGACAGTACCTTCGCTTCTCAC (SEQ ID NO: 22) |
| DSD-2 | ACAGGTCCGTAAAGGATGCGGCATGCATAGGTTGGTTG (SEQ ID NO: 23) |
| DSD-3 | CGCATCCTTTACGGACCTGTCCTATCCACAGGGTTTTCAC (SEQ ID NO: 24) |
| 106V-2 | GCCTGCTTCACGTCTTTATTCTTGTATGACTCTCC (SEQ ID NO: 25) |
| 106V-3 | GAATAAAGACGTGAAGCAGGCCTTCTTTTATC (SEQ ID NO: 26) |
| 56A-2 | GGGTTTTCGGCATCAGCAGCGTAGATGCCA (SEQ ID NO: 27) |
| 56A-3 | GCTGCTGATGCCGAAAACCCCTATTACGATGAC (SEQ ID NO: 28) |
| 56C-2 | GGGTTTTCGCAATCAGCAGCGTAGATGCCA (SEQ ID NO: 29) |
| 56C-3 | GCTGCTGATTGCGAAAACCCCTATTACGATGAC (SEQ ID NO: 30) |
| 56D-2 | GGGTTTTCGTCATCAGCAGCGTAGATGCCA (SEQ ID NO: 31) |
| 56D-3 | GCTGCTGATGACGAAAACCCCTATTACGATGAC (SEQ ID NO: 32) |
| 56E-2 | GGGTTTTCCTCATCAGCAGCGTAGATGCCA (SEQ ID NO: 33) |
| 56E-3 | GCTGCTGATGAGGAAAACCCCTATTACGATGAC (SEQ ID NO: 34) |
| 56F-2 | GGGTTTTCGAAATCAGCAGCGTAGATGCCA (SEQ ID NO: 35) |
| 56F-3 | GCTGCTGATTTCGAAAACCCCTATTACGATGAC (SEQ ID NO: 36) |
| 56G-2 | GGGTTTTCACCATCAGCAGCGTAGATGCCA (SEQ ID NO: 37) |
| 56G-3 | GCTGCTGATGGTGAAAACCCCTATTACGATGAC (SEQ ID NO: 38) |
| 56H-2 | GGTTTTCATGATCAGCAGCGTAGATGCCAT (SEQ ID NO: 39) |
| 56H-3 | CGCTGCTGATCATGAAAACCCCTATTACGATGAC (SEQ ID NO: 40) |
| 56I-2 | GGGTTTTCGATATCAGCAGCGTAGATGCCA (SEQ ID NO: 41) |
| 56I-3 | GCTGCTGATATCGAAAACCCCTATTACGATGAC (SEQ ID NO: 42) |
| 56K-2 | AGGGGTTTTCCTTATCAGCAGCGTAGATGCCAT (SEQ ID NO: 43) |
| 56K-3 | CGCTGCTGATAAGGAAAACCCCTATTACGATGAC (SEQ ID NO: 44) |
| 56L-2 | GGGTTTTCCAAATCAGCAGCGTAGATGCCA (SEQ ID NO: 45) |
| 56L-3 | GCTGCTGATTTGGAAAACCCCTATTACGATGAC (SEQ ID NO: 46) |
| 56M-2 | GGGTTTTCCATATCAGCAGCGTAGATGCCA (SEQ ID NO: 47) |
| 56M-3 | GCTGCTGATATGGAAAACCCCTATTACGATGAC (SEQ ID NO: 48) |
| 56N-2 | GGTTTTCGTTATCAGCAGCGTAGATGCCAT (SEQ ID NO: 49) |
| 56N-3 | CGCTGCTGATAACGAAAACCCCTATTACGATGAC (SEQ ID NO: 50) |
| 56P-2 | GGGTTTTCTGGATCAGCAGCGTAGATGCCA (SEQ ID NO: 51) |
| 56P-3 | GCTGCTGATCCAGAAAACCCCTATTACGATGAC (SEQ ID NO: 52) |
| 56Q-2 | GGGTTTTCTTGATCAGCAGCGTAGATGCCA (SEQ ID NO: 53) |
| 56Q-3 | GCTGCTGATCAAGAAAACCCCTATTACGATGAC (SEQ ID NO: 54) |
| 56R-2 | AGGGGTTTTCTCTATCAGCAGCGTAGATGCCAT (SEQ ID NO: 55) |
| 56R-3 | CGCTGCTGATAGAGAAAACCCCTATTACGATGAC (SEQ ID NO: 56) |
| 56S-2 | GGTTTTCAGAATCAGCAGCGTAGATGCCAT (SEQ ID NO: 57) |
| 56S-3 | CGCTGCTGATTCTGAAAACCCCTATTACGATGAC (SEQ ID NO: 58) |
| 56T-2 | GGGTTTTCGGTATCAGCAGCGTAGATGCCA (SEQ ID NO: 59) |
| 56T-3 | GCTGCTGATACCGAAAACCCCTATTACGATGAC (SEQ ID NO: 60) |

TABLE 1-continued

| Primer Name | Primer Sequence 5'-3' |
|---|---|
| 56V-2 | GGGTTTTCGACATCAGCAGCGTAGATGCCA (SEQ ID NO: 61) |
| 56V-3 | GCTGCTGATGTCGAAAACCCCTATTACGATGAC (SEQ ID NO: 62) |
| 56W-2 | GGGTTTTCCCAATCAGCAGCGTAGATGCCA (SEQ ID NO: 63) |
| 56W-3 | GCTGCTGATTGGGAAAACCCCTATTACGATGAC (SEQ ID NO: 64) |
| 20H-2 | TATCAATGGCATGGTTCACGATCCATAAGTGAC (SEQ ID NO: 65) |
| 20H-3 | GGATCGTGAACCATGCCATTGATATAATGTCTAGG (SEQ ID NO: 66) |
| 83D-2 | CTTAGCTTGCTTGTCGAATGGGATATATGTCTTTCCG (SEQ ID NO: 67) |
| 83D-3 | ATCCCATTCGACAAGCAAGCTAAGGAGACTG (SEQ ID NO: 68) |

Example 1: Construction and Screening of Mutant Library PLC-N63DN131SN134D

BC-PC-PLC DNA sequence (SEQ ID NO: 8, its encoded amino acid sequence is set forth in SEQ ID NO: 9) is designed according to the mature peptide sequence of *Bacillus cereus* phosphatidylcholine-specific phospholipase C (PDB ID: 1AH7) and *Pichia* codon preference, which has a factor signal peptide sequence and a *Pichia* Kozak sequence fused at its front end, and eventually α-BC-PC-PLC DNA sequence (SEQ ID NO: 10) is obtained.

The α-BC-PC-PLC DNA sequence is sent to Shanghai Sangon Biological Co., Ltd. for total gene synthesis to give a cloning vector pGEM-T-PLC containing α-BC-PC-PLC DNA sequence. PLC fragment is amplified by PCR with this vector as the template, using PrimeSTAR® HS DNA Polymerase and primer pair AmPLC-3/AmPLC-4.

AOX1 promoter fragment (PAOX1) is amplified by PCR with pPIC-9k expression vector as the template, using PrimeSTAR® HS DNA Polymerase and primer pair AmPLC-1/AmPLC-2.

PAOX1+PLC fusion fragment is obtained by overlap PCR using primer pair AmPLC-1/AmPLC-4 and PrimeSTAR® HS DNA Polymerase. PAOX1+PLC pAO815 fusion fragment is cloned into the vector using AatII and EcoRI restriction sites to give the expression vector pAO-PLC.

pAO-PLC is linearized with SalI, a 8.5 kb fragment is recovered by gel. Competent cells of *Pichia pastoris* GS115 strain is prepared with LiAC method, and then transformed with linearized pAO-PLC fragment by electroporation. The transformant is plated on MGYS plates and cultured at 30° C. for 3 days. The monoclonal colony on the plate is picked into 5 μL sterile water, of which 0.5 μL is taken and loaded on a BMM-soybean phospholipid screening plate. After incubation at 30° C. for 3 days, positive clones may be observed with a white precipitating ring around the thalli, a positive strain is screened and named PLC-WT.

A fragment of about 900 bp is obtained by PCR amplification with pAO-PLC vector as the template, using PrimeSTAR® HS DNA Polymerase and primer pair AmPLC-1/AOXH-2. A fragment of about 1.1 kb is obtained by PCR amplification with pAO-PLC vector as the template, using PrimeSTAR® HS DNA Polymerase and primer pair AOXH-3/AmPLC-4, and a fragment of about 1.9 kb is obtained with PCR amplification by mixing the previous obtained fragments of about 900 bp and about 1.1 kb as the template in the third step of PCR, using primer pair AmPLC-1/AmPLC-4 and PrimeSTAR® HS DNA Polymerase.

The fragment of about 1.9 kb is cloned into pAO-PLC at AatII and EcoRI restriction sites to give pmAO-PLC. In pmAO-PLC, a HindIII restriction site in pAO-PLC is mutated, thereby leaving a HindIII restriction site only at 5' end of BC-PC-PLC sequence, so that HindIII and EcoRI may be used to clone BC-PC-PLC mutated fragment into pmAO-PLC.

A fragment of about 207 bp is obtained by PCR amplification with pAO-PLC vector as the template, using PrimeSTAR® HS DNA Polymerase and primer pair EPPLC-1/63D-2. A fragment of about 576 bp is obtained by PCR amplification with pAO-PLC vector as the template, using PrimeSTAR® HS DNA Polymerase and primer pair 63D-3/EPPLC-2, and a fragment of about 755 bp is obtained with PCR amplification by mixing the previous obtained fragments of about 207 bp and about 576 bp as the template in the third step of PCR, using primer pair EPPLC-1/EPPLC-2 and PrimeSTAR® HS DNA Polymerase. The 755 bp fragment is cloned into pmAO-PLC by HindIII and EcoRI restriction sites to give vector pmAO-PLC-N63D.

A fragment of about 414 bp is obtained by PCR amplification with pmAO-PLC-N63D vector as the template, using PrimeSTAR® HS DNA Polymerase and primer pair EPPLC-1/DSD-2 (sequence in Table 1). A fragment of about 361 bp is obtained by PCR amplification with pAO-PLC vector as the template, using PrimeSTAR® HS DNA Polymerase and primer pair DSD-3/EPPLC-2 (sequence in Table 1). A fragment of 755 bp is obtained with PCR amplification by mixing the previous obtained fragments of 414 bp and 361 bp as the template, using primer pair EPPLC-1/EPPLC-2 and PrimeSTAR® HS DNA Polymerase. The 755 bp fragment is cloned into pmAO-PLC by HindIII and EcoRI restriction sites to give pmAO-PLC-N63DN131SN134D vector.

Error-prone PCR (0.3 mM MnCl$_2$ is additionally added during PCR) is performed with pmAO-PLC-N63DN131SN134D vector as the template, using TaKaRa Taq enzyme and primer pair EPPLC-1/EPPLC-2 to give a collection of mutant amplicons with a size of about 755 bp. The obtained fragment is cloned into pmAO-PLC by HindIII and EcoRI restriction sites, and the resultant vector is transformed into *E. coli* DH5a strain to give a total of 1×10$^4$ BC-PC-PLC mutants.

1×10$^3$ PLC-N63DN131SN134D mutant is washed with 2 ml sterile water to 8 ml liquid LB medium (containing 100 μg/ml ampicillin) and cultured at 37° C. for 4 hours. plasmid is extracted, linearized with SalI, with a fragment of about 8.5 kb recovered. Take 500 ng vector (DNA is used in a minimum amount as possible to ensure that most positive transformants contain a single copy of PLC gene), the vector is transformed into competent cells of *Pichia pastoris* GS115 strain by electrotransformation. The transformant is plated onto MGYS plates, cultured at 30° C. for 3 days to obtain PLC-N63DN131SN134D *Pichia* mutant library. A single clone is picked from the plate, and plated to a BMM-soybean phospholipid screening plate. The clone with a large white halo is selected. The clone is numbered #31.

Example 2: PLC-N63DN131SN134D Mutant Sequence Analysis

The #31 strain is plated on 3 ml YPD liquid medium, cultured at 30° C. overnight, and genomic DNA is extracted. PLC DNA sequence in the #31 strain is obtained by PCR amplification with #31 strain genomic DNA as the template, using PrimeSTAR® HS DNA Polymerase and primer pair AOX1-5/AOX1-3 PCR. The obtained sequence is sent to the Shanghai Sangon Biological Co., Ltd. for sequencing with primer pair AOX1-5/AOX1-3. Sequencing results of the PLC DNA in #31 show two mutated bases, tyrosine at position 56 is mutated to histidine (TAT→CAT); and methionine at position 106 is mutated to valine (ATG-→GTG). The sequence is set forth in SEQ ID NO: 3.

Example 3: Construction and Screening of PLC-N63DN131SN134D Single Point Mutant *Pichia* Expression Strain 1. Construction and Screening of PLC-N63DN131SN134D-Y56H A fragment of about 180 bp is obtained by PCR amplification with pmAO-PLC-N63DN131SN134D vector as the template, using PrimeSTAR® HS DNA Polymerase and primer pair EPPLC-1/56H-2. A fragment of about 570 bp is obtained by PCR amplification with pmAO-PLC-N63DN131SN134D vector as the template, using PrimeSTAR® HS DNA Polymerase and primer pair 56H-3/EPPLC-2. A fragment of about 755 bp is obtained with PCR amplification by mixing thepreviously obtained two-step PCR fragments of about 180 bp and about 570 bp as the template in a third step, using primer pair EPPLC-1/EPPLC-2 and PrimeSTAR® HS DNA Polymerase.

The fragment of about 755 bp is cloned into pmAO-PLC by HindIII and EcoRI restriction sites to give pmAO-PLC-N63DN131SN134D-Y56H vector. The pmAO-PLC-N63DN131SN134D-Y56H is linearized with SalI, an 8.5 kb fragment is obtained by gel recovery. Competent cells of *Pichia* yeast strain SMD1168 are prepared by LiAC method, and then 500 ng linearized pmAO-PLC-N63DN131SN134D-Y56H is transformed into the competent cells of SMD1168 by electroporation. The transformant is plated onto MGYS plates and cultured at 30° C. for 3 days. A single clone is picked on the plate, and plated to a BMM-soybean phospholipid screening plate. The clone with a large white halo is selected.

2. Construction and Screening of PLC-N63DN131SN134D-M106V

A fragment of about 320 bp is obtained by PCR amplification with pmAO-PLC-N63DN131SN134D vector as the template, using PrimeSTAR® HS DNA Polymerase and primer pair EPPLC-1/106V-2. A fragment of about 440 bp is obtained by PCR amplification with pmAO-PLC-N63DN131SN134D vector as the template, using PrimeSTAR® HS DNA Polymerase and primer pair 106V-3/EPPLC-2. Then a fragment of about 755 bp is obtained by PCR amplification with the fragments of about 320 bp and about 440 bp obtained in the previous two-step PCR mixed as the template for PCR in a third step, using primer pair EPPLC-1/EPPLC-2 and PrimeSTAR® HS DNA Polymerase.

The fragment of about 755 bp is cloned into pmAO-PLC by HindIII and EcoRI restriction sites to give pmAO-PLC-N63DN131SN134D-M106V vector. pmAO-PLC-N63DN131SN134D-M106V is linearized with SalI, a 8.5 kb fragment is obtained by gel recovery. Competent cells of *Pichia* yeast strain SMD1168 is prepared by LiAC method, then 500 ng linearized pmAO-PLC-N63DN131SN134D-M106V is transformed into the competent cells of SMD1168 by electroporation. The transformant is plated onto MGYS plates and cultured at 30° C. for 3 days. A single clone is picked on the plate, and plated to a BMM-soybean phospholipid screening plate. The clone with a large white halo is selected.

3. Construction and Screening of PLC-N63DN131SN134D-Y56HM106V

A fragment of about 755 bp is obtained by PCR amplification with #31 strain genomic DNA as the template, using PrimeSTAR® HS DNA Polymerase and primer pair EPPLC-1/EPPLC-2. The fragment of about 755 bp is cloned into pmAO-PLC by HindIII and EcoRI restriction sites to give pmAO-N63DN131SN134D-Y56HM106V vector. pmAO-7-7PLC-106M is linearized with SalI, a 8.5 kb fragment is obtained by gel recovery. Competent cells of *Pichia* yeast strain SMD1168 is prepared by LiAC method, and then 500 ng linearized pmAO-N63DN131SN134D-Y56HM106V is transformed into competent cells of SMD1168 by electroporation. The transformant is plated onto MGYS plates and cultured at 30° C. for 3 days. A single clone is picked on the plate, and plated to a BMM-soybean phospholipid screening plate. The clone with a large white halo is selected.

As shown in FIG. 1, when the size of white halos on the BMM-soybean phospholipid screening plate for three mutants PLC-N63DN131SN134D-Y56H, PLC-N63DN131SN134D-M106V and PLC-N63DN131SN134D-Y56HM106V is compared, it is found that PLC-N63DN131SN134D-Y56H and PLC-N63DN131SN134D-Y56HM106V have a comparative size of white halo, and PLC-N63DN131SN134D-M106V has a size of white halo significantly smaller than PLC-N63DN131SN134D-Y56H and PLC-N63DN131SN134D-Y56HM106V, indicating that Y56H mutation further improves the activity of the mutant and Y56H is a critical mutation site.

Example 4: Saturation Mutation of Amino Acid at Position 56 of PLC-N63DN131SN134D The tyrosine at position 56 of PLC-N63DN131SN134D is mutated to alanine (A), cysteine (C), aspartic acid (D), glutamic acid (E), phenylalanine (F), glycine (G), histidine (H), isoleucine (the I), lysine (K), leucine (L), methionine (M), asparagine (N), proline (P), glutamine (Q), arginine (R), threonine (T), valine (V) and tryptophan (W), respectively.

Briefly, a fragment of about 180 bp is obtained by PCR amplification with pmAO-PLC-N63DN131SN134D vector as the template, using PrimeSTAR® HS DNA Polymerase and primer pair EPPLC-1/56X-2 (X refers to the one-letter abbreviation of above 18 amino acids). A fragment of about 570 bp is obtained by PCR amplification with pmAO-PLC-N63DN131SN134D vector as the template, using PrimeSTAR® HS DNA Polymerase and primer pair 56X-3/EP- PLC-2. A fragment of about 755 bp is obtained by PCR amplification with the mixed previously obtained two-step PCR fragments of about 180 bp and about 570 bp as the template in a third step, using primer pair EPPLC-1/EP-PLC-2 and PrimeSTAR® HS DNA Polymerase.

The 18 resultant fragments about 755 bp are cloned into pmAO-PLC by HindIII and EcoRI restriction sites, respectively, to obtain 18 pmAO-7-7PLC-Y56X vectors, which are linearized with SalI, and an 8.5 kb fragment is obtained by gel recovery. Competent cells of *Pichia* yeast strain SMD1168 is prepared by LiAC method, and then 500 ng of each one of the 18 linearized pmAO-PLC-N63DN131SN134D-Y56X is transformed into the competent cells of SMD1168 by electroporation. The transformant is plated onto MGYS plates and cultured at 30° C. for 3 days. A single clone is picked on the plate, and plated to a BMM-soybean phospholipid screening plate. The clone with a large white halo is selected.

PLC-WT, PLC-N63DN131SN134D and PLC-N63DN131SN134D strains with saturation mutation at position 56 are picked and first activated in liquid YPD, and then inoculated into BMGY medium and subjected to 220 rpm shaking at 30° C. overnight. The culture is transferred to BMMY medium with an initial OD600 of 6.

First, induction is performed with 2% methanol, supplemented with 1% methanol after 24 h and 32 h, supplemented with 1% methanol after 48 h and 56 h, and sampled at 72 h. The obtained samples are ultrafiltration desalted and concentrated 20-fold using a ultrafiltration device with a molecular weight cutoff of 10 kDa. The treated samples are added to a buffer (20 mM citric acid-sodium citrate buffer (pH 6.6), 10 uM $ZnSO_4$).

1 μl of fermentation broth is added to 190 μl of PLC reaction solution (containing 0.5% soybean phospholipid, 25 mM citric acid-sodium citrate buffer solution pH 6.6, 10 uM $ZnSO_4$) and incubated with shaking at 45° C. for 30 minutes. After incubation, 100 μl of chloroform is added followed by oscillation mixing, centrifugation at 12000 rpm for 2 minutes. 80 μl of supernatant is taken and 20 μl of CIAP reaction solution (containing 50 mM Tris-HCl pH 9.0, 10 mM $MgCl_2$, 1 U CIAP) is added and incubated at 37° C. for 1 h.

Figure 2:
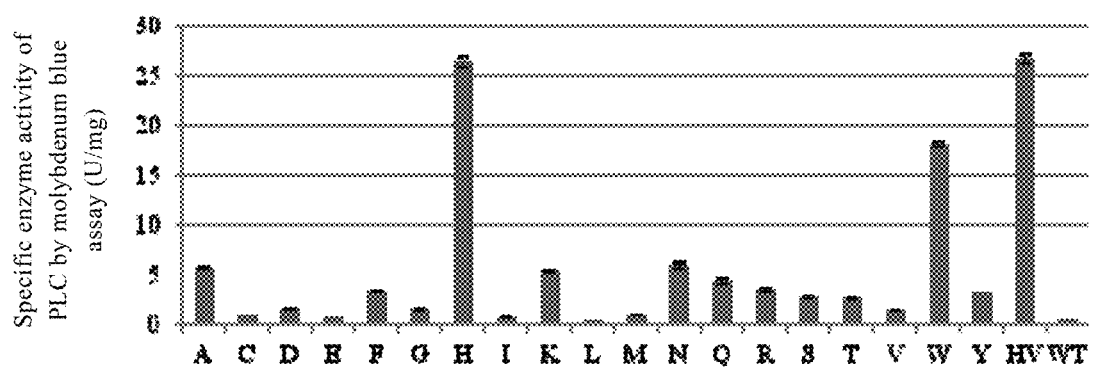
FIG. 2 shows the specific activity of each mutant.

After incubation, 100 μl reaction is taken, and 900 μl of molybdenum blue development solution (containing 0.2% ascorbic acid, 0.1% ammonium molybdate) is added and incubated with shaking at 37° C. for 10 minutes. Absorbance of the samples at a wavelength of 700 nm is measured and calculated to obtain PLC activity of each broth sample. The protein concentration in the fermentation broth of PLC-N63DN131SN134D and PLC-N63DN131SN134D strains with saturation mutation at position 56 is determined using the Bradford reagent to obtain the specific enzyme activity. As shown in FIG. 2, the specific enzyme activities of PLC-N63DN131SN134D-Y56H and PLC-N63DN131SN134D-Y56W have a 7-fold and 5-fold increase compared to that of PLC-N63DN131SN134D, respectively.

Figure 3:
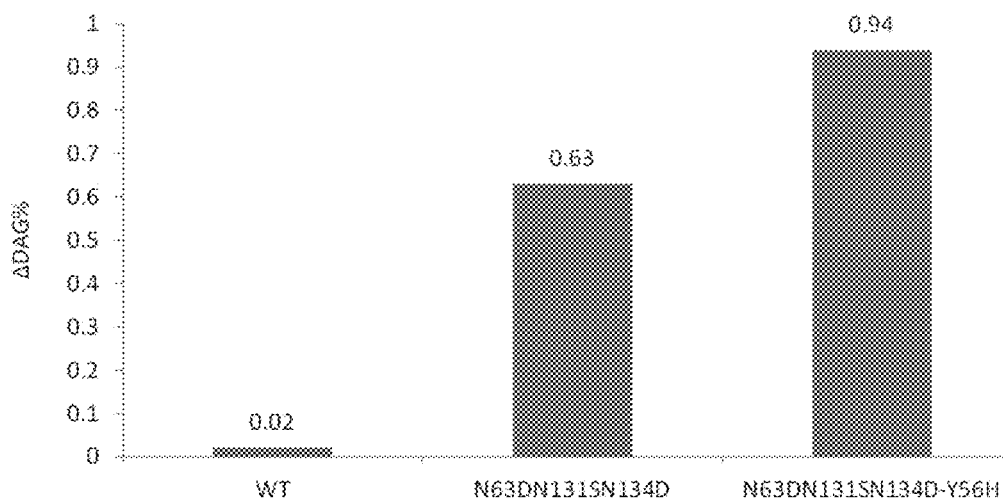
FIG. 3 shows the test results of N63DN131SN134D and N63DN131SN134D-Y56H degumming.
Figure 4:
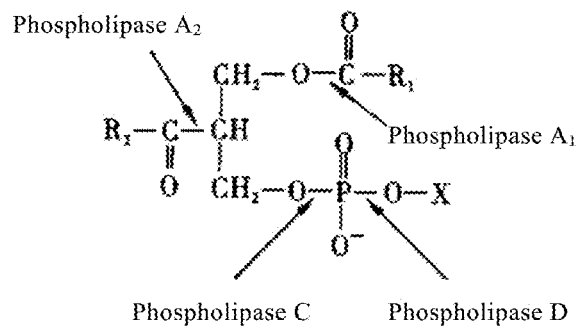
FIG. 4 shows the site of action on the phospholipid molecule for various phospholipases.

Example 5: PLC-N63DN131SN134D-Y56H Degumming Test 100 g of soybean crude oil is taken and heated to 55° C., 200 ppm of PLC-WT, PLC-N63DN131SN134D sample and PLC-N63DN131SN134D-Y56H are added to obtain 3% aqueous phase in the system, high sheared using high-speed shearing machine (10000 r/min) for 1 minute, and the reaction is stirred (750 r/min) at 55° C. for 2 h and heated to 85° C. for 5 min. The samples are centrifuged at 12000 rpm for 10 min, approximately 10 g of the upper oil sample is taken and the DAG content thereof is detected by HPLC (determined by the method of AOCS Cd 11d-96(09)). The DAG increase for PLC-N63DN131SN134D sample and PLC-N63DN131SN134D-Y56H compared to crude oil is shown in FIG. 3, and the DAG increase for PLC-N63DN131SN134D-Y56H is 1.5 times of the PLC-N63DN131SN134D.

Example 6: Mutated Sequence and its Activity

A fragment of about 78 bp is obtained by PCR amplification with pmAO-PLC-N63DN131SN134D vector as the template, using PrimeSTAR® HS DNA Polymerase and primer pair EPPLC-1/20H-2. A fragment of about 707 bp is obtained by PCR amplification with pmAO-PLC-N63DN131SN134D vector as the template, using PrimeSTAR® HS DNA Polymerase and primer pair 20H-3/EP-PLC-2. A fragment of about 755 bp is obtained by PCR amplification with the previously obtained two-step PCR fragments of about 78 bp and about 707 bp mixed as the template in a third step, using primer pair EPPLC-1/EP-PLC-2 and PrimeSTAR® HS DNA Polymerase.

The fragment of about 755 bp is cloned into pmAO-PLC by HindIII and EcoRI restriction sites to give pmAO-PLC-N63DN131SN134D-R20H vector. pmAO-PLC-N63DN131SN134D-R20H is linearized with SalI, and a 8.5 kb fragment is obtained by gel recovery. Competent cells of *Pichia* yeast strain SMD1168 is prepared by LiAC method, and then 500 ng linearized pmAO-PLC-N63DN131SN134D-R20H is transformed into the competent cells of SMD1168 by electroporation. The transformant is plated onto MGYS plates and cultured at 30° C. for 3 days. A single clone is picked on the plate, and plated to a BMM-soybean phospholipid screening plate. The clone with a large white halo is selected as PLC-N63DN131SN134D-R20H.

A fragment of about 266 bp is obtained by PCR amplification with pmAO-PLC-N63DN131SN134D vector as the template, using PrimeSTAR® HS DNA Polymerase and primer pair EPPLC-1/83D-2. A fragment of about 520 bp is obtained by PCR amplification with pmAO-PLC-N63DN131SN134D vector as the template, using PrimeSTAR® HS DNA Polymerase and primer pair 83D-3/EP-PLC-2. A fragment of about 755 bp is obtained by PCR amplification with the previously obtained two-step PCR fragments of about 266 bp and about 520 bp mixed as the template in a third step, using primer pair EPPLC-1/EP-PLC-2 and PrimeSTAR® HS DNA Polymerase.

The fragment of about 755 bp is cloned into pmAO-PLC by HindIII and EcoRI restriction sites to give pmAO-PLC-N63DN131SN134D-A83D vector. pmAO-PLC-N63DN131SN134D-A83D is linearized with SalI, and a 8.5 kb fragment is obtained by gel recovery. Competent cells of *Pichia* yeast strain SMD1168 is prepared by LiAC method, and then 500 ng linearized pmAO-PLC-N63DN131SN134D-A83D is transformed into the competent cells of SMD1168 by electroporation. The transformant is plated onto MGYS plates and cultured at 30° C. for 3 days. A single clone is picked on the plate, and plated to a BMM-soybean phospholipid screening plate. The clone with a large white halo is selected as PLC-N63DN131SN134D-A83D.

PLC-N63DN131SN134D, PLC-N63DN131SN134D-R20H and PLC-N63DN131SN134D-A83D strains are taken and first activated in liquid YPD, and then inoculated into BMGY medium and subjected to 220 rpm shaking at 30° C. overnight. The culture is transferred to BMMY medium with an initial OD600 of 6.

First, induction is performed with 2% methanol, supplemented with 1% methanol after 24 h and 32 h, supplemented with 1% methanol after 48 h and 56 h, and sampled at 72 h. Obtained samples are ultrafiltration desalted and concentrated 20-fold using an ultrafiltration device with a molecular weight cutoff of 10 kDa. The treated samples are added to a buffer (20 mM citric acid-sodium citrate buffer (pH 6.6), 10 uM $ZnSO_4$).

1 µl of fermentation broth is added to 190 µl of PLC reaction solution (containing 0.5% soybean phospholipid, 25 mM citric acid-sodium citrate buffer solution pH 6.6, 10 uM $ZnSO_4$) and incubated with shaking at 45° C. for 30 minutes. After incubation, 100 µl of chloroform is added followed by oscillation mixing, centrifugation at 12000 rpm for 2 minutes. 80 µl supernatant is taken and 20 µl CIAP reaction solution (containing 50 mM Tris-HCl pH 9.0, 10 mM $MgCl_2$, 1 U CIAP) is added and incubated at 37° C. for 1 h.

After incubation, 100 µl reaction is taken, and 900 µl molybdenum blue development solution (containing 0.2% ascorbic acid, 0.1% ammonium molybdate) is added and incubated with shaking at 37° C. for 10 minutes. Absorbance of the samples at a wavelength of 700 nm is measured and calculated to obtain PLC activity of each broth sample. The protein concentration in the fermentation broth of PLC-N63DN131SN134D, PLC-N63DN131SN134D-R20H and PLC-N63DN131SN134D-A83D is determined using the Bradford reagent to obtain the specific enzyme activity. There is no significant difference among these three in terms of specific enzyme activity.

Example 7

100 g of Soybean crude oil is taken and heated to 55° C.; samples of phospholipase C (one of SEQ ID SEQ ID NO: 7, wherein Xaa is His) are diluted by 100-fold; 1 ml water and 2 ml diluted phospholipase C samples are added (3% water addition, enzyme is added in 200 ppm); high shear (10000 r/min) for 1 minute; stirred at 55° C. (750 r/min) for 2 hours; heated to 85° C. for 5 min; and centrifuged at 12000 rpm for 10 minutes, approximately 10 g of the upper layer of oil samples is taken and its DAG content is detected (detection method: AOCS Official method Cd 11d-96). After calculation, the increase ΔDAG of diglyceride in the degummed soybean oil is 1.02%.

Example 8

Samples of phospholipase C (one of SEQ ID NO: 7, wherein Xaa is His) are diluted 10-fold and placed in a water bath at 50° C. for 0.5 hour.

100 g of Soybean crude oil is taken and heated to 55° C.; samples of phospholipase C are diluted by 10-fold; 1 ml water and 2 ml diluted phospholipase C samples are added (3% water addition, enzyme is added in 200 ppm); high shear (10000 r/min) for 1 minute; stirred at 55° C. (750 r/min) for 2 hours; heated to 85° C. for 5 min; and centrifuged at 12000 rpm for 10 minutes, approximately 10 g of the upper layer of oil samples is taken and its DAG content is detected (detection method: AOCS Official method Cd 11d-96). After calculation, the increase ΔDAG of diglyceride in the degummed soybean oil is 1.02%.

Example 9

Samples of phospholipase C (one of SEQ ID NO: 7, wherein Xaa is His) are diluted 10-fold and placed in a water bath at 60° C. for 0.5 hour.

100 g of Soybean crude oil is taken and heated to 55° C.; samples of phospholipase C are diluted by 10-fold; 1 ml water and 2 ml diluted phospholipase C samples are added (3% water addition, enzyme is added in 200 ppm); high shear (10000 r/min) for 1 minute; stirred at 55° C. (750 r/min) for 2 hours; heated to 85° C. for 5 min; and centrifuged at 12000 rpm for 10 minutes, approximately 10 g of the upper layer of oil samples is taken and its DAG content is detected (detection method: AOCS Official method Cd 11d-96). After calculation, the increase ΔDAG of diglyceride in the degummed soybean oil is 1.06%.

Example 10

Samples of phospholipase C (one of SEQ ID NO SEQ ID NO: 7, wherein Xaa is His) are diluted 10-fold and placed in a water bath at 70° C. for 0.5 hour.

100 g of Soybean crude oil is taken and heated to 55° C.; samples of phospholipase C are diluted by 10-fold; 1 ml water and 2 ml diluted phospholipase C samples are added (3% water addition, enzyme is added in 200 ppm); high shear (10000 r/min) for 1 minute; stirred at 55° C. (750 r/min) for 2 hours; heated to 85° C. for 5 min; and centrifuged at 12000 rpm for 10 minutes, approximately 10 g of the upper layer of oil samples is taken and its DAG content is detected (detection method: AOCS Official method Cd 11d-96). After calculation, the increase ΔDAG of diglyceride in the degummed soybean oil is 1.11%.

Example 11

Samples of phospholipase C (one of SEQ ID NO SEQ ID NO: 7, wherein Xaa is His) are diluted 10-fold and placed in a water bath at 80° C. for 0.5 hour.

100 g of Soybean crude oil is taken and heated to 55° C.; samples of phospholipase C are diluted by 10-fold; 1 ml water and 2 ml diluted phospholipase C samples are added (3% water addition, enzyme is added in 200 ppm); high shear (10000 r/min) for 1 minute; stirred at 55° C. (750 r/min) for 2 hours; heated to 85° C. for 5 min; and centrifuged at 12000 rpm for 10 minutes, approximately 10 g of the upper layer of oil samples is taken and its DAG content is detected (detection method: AOCS Official method Cd 11d-96). After calculation, the increase ΔDAG of diglyceride in the degummed soybean oil is 0.73%.

Example 12: Construction of pAO-PLC

A fragment of about 750 bp is obtained by PCR amplification with BC-PC-PLC gene (which encodes the amino acid sequence as set forth in SEQ ID NO: 4) as the template, using PrimeSTAR® HS DNA Polymerase and primer pair PLC-F/PLC-R (Table 2 below). The fragment of about 750 bp is cloned into pAO-PLC by HindIII and EcoRI restriction sites to give vector pAO-PLC.

Example 13: Obtaining Albumin Signal Sequence from *Homo sapiens* and Killer Protein Signal Sequence from *Saccharomyces cerevisiae*

The nucleotide sequence and amino acid sequence of albumin signal sequence from *Homo sapiens* are:

```
                                              (SEQ ID NO: 69)
ATGAAGTGGGTTACCTTTATCTCTTTGTTGTTTCTTTTCTCTTCT
GCTTACTCT
```
and

```
                                              (SEQ ID NO: 70)
MKWVTFISLLFLFSSAYS.
```

The nucleotide sequence and amino acid sequence of killer protein signal sequence from *Saccharomyces cerevisiae* are:

```
                                              (SEQ ID NO: 71)
ATGACTAAGCCAACCCAAGTATTAGTTAGATCCGTCAGTATATTA
TTTTTCATCACATTACTACATCTAGTCGTAGCT
```
and

```
                                              (SEQ ID NO: 72)
MTKPTQVLVRSVSILFFITLLHLVVA.
```

With pAO-PLC gene as the template, PrimeSTAR® HS DNA Polymerase enzyme and primer pair (see Table 2) are used, with the primers for albumin signal peptide are: S4-1F, S4-2F, S4-3F, S4-4F/PLC-R, and the primers for killer protein signal sequence are: S7-1F, S7-2F, S7-3F, S7-4F, S7-5F/PLC. Using overlap PCR, a signal peptide fusion fragment BC-PC-PLC gene is obtained (with AvrII, EcoRI restriction sites added at both ends).

TABLE 2

Primer sequence for signal peptide
(SEQ ID NOs: 73-83)

| Primer Name | Sequence |
| --- | --- |
| S4-1F | GCGCCTAGGCCGCGGCGAAACGATGAAGTGGGTTACCT |
| S4-2F | CGATGAAGTGGGTTACCTTTATCTCTTTGTTGTTTCT |
| S4-3F | TTATCTCTTTGTTGTTTCTTTTCTCTTCTGCTTACTC |
| S4-4F | TTTCTCTTCTGCTTACTCTGCTCCAGTCAACACTACA |
| S7-1F | GCGCCTAGGCCGCGGCGAAACGATGACTAAGCCAACCC |
| S7-2F | CGATGACTAAGCCAACCCAAGTATTAGTTAGATCCGTC |
| S7-3F | GTATTAGTTAGATCCGTCAGTATATTATTTTTCATCAC |
| S7-4F | TATATTATTTTTCATCACATTACTACATCTAGTCGTAG |
| S7-5F | TACTACATCTAGTCGTAGCTGCTCCAGTCAACACTACA |
| PLC-F | CTGAAGCTTGGTCAGCTGAGGACAAGCAT |
| PLC-R | CCGGAATTCTTACCTGTCACCGTAAGTGTCGAACCATA |

Example 14: Construction and Screening of *Pichia pastoris* Expression Strains of which the Expression is Driven by Three Different Signal Peptides 1. Construction and Screening of pAO-PLC pAO-PLC vector is constructed as Example 12. pAO-PLC is linearized with SalI, a 8.5 kb fragment is obtained by gel recovery. Competent cells of *Pichia* yeast strain SMD1168 are prepared by LiAC method, and then 500 ng linearized pAO-PLC is transformed into the competent cells of SMD1168 by electroporation. The transformant is plated onto MGYS plates and cultured at 30° C. for 3 days. A single colony picked on the plate, and plated to a BMM-soybean phospholipid screening plate. The clone with a large white halo is selected to obtain a strain wherein expression of phospholipase C is driven by α-mating factor signal peptide (having a nucleotide sequence as position 8 to 64 of SEQ ID NO: 64).

2. Construction and Screening of pAO4-PLC

A fragment of about 750 bp is obtained by overlap PCR amplification with pAO-PLC vector as the template, using PrimeSTAR® HS DNA Polymerase and primer pair S4-1F, S4-2F, S4-3F, S4-4F/PLC-R, amplified by overlap PCR. The fragment is a fragment of albumin signal sequence from *Homo sapiens* fused with BC-PC-PLC gene (with AvrII, EcoRI restriction sites added at both ends).

This fragment is cloned into pAO815 by EcoRI and AvrII restriction sites to give pAO4-PLC vector. pAO4-PLC is linearized with SalI, a 8.5 kb fragment is obtained by gel recovery. Competent cells of *Pichia* yeast strain SMD1168 are prepared by LiAC method, and then 500 ng linearized pAO4-PLC is transformed into the competent cells of SMD1168 by electroporation. The transformant is plated onto MGYS plates and cultured at 30° C. for 3 days. A single clone is picked on the plate, and plated to a BMM-soybean phospholipid screening plate. The clone with a large white halo is selected to obtain a strain wherein expression of phospholipase C is derived by albumin signal sequence from *Homo sapiens*.

3. Construction and Screening of pAO7-PLC

A fragment of about 750 bp is obtained by overlap PCR amplification with pAO-PLC vector as the template, PrimeSTAR® HS DNA Polymerase and primer pair S7-1F, S7-2F, S7-3F, S7-4F, S7-5F/PLC, the fragment is a fragment of killer protein signal sequence from *Saccharomyces cerevisiae* fused with BC-PC-PLC gene (with AvrII, EcoRI restriction sites added at both ends).

This fragment is cloned into pAO-815 by EcoRI and AvrII restriction sites to give pAO7-PLC vector. pAO7-PLC is linearized with SalI, a 8.5 kb fragment is obtained by gel recovery. Competent cells of *Pichia* yeast strain SMD1168 are prepared by LiAC method, and then 500 ng linearized pAO7-PLC is transformed into the competent cells of SMD1168 by electroporation. The transformant is plated onto MGYS plates and cultured at 30° C. for 3 days. A single clone is picked on the plate, and plated to a BMM-soybean phospholipid screening plate. The clone with a large white halo is selected to obtain a strain wherein expression of phospholipase C is driven by killer protein signal sequence from *Saccharomyces cerevisiae*.

Example 15: Fermantion of *Pichia pastoris* Expression Strains of which the Expression is Driven by Three Different Signal Peptides and Detection of Enzymatic Activity Thereof Strains of which the expression is driven by three different signal peptides are taken, activated in liquid YPD, and then inoculated into BMGY medium and subjected to 220 rpm shaking at 30° C. overnight. The culture is transferred to BMMY medium with an initial OD600 of 6. Induction is performed with 2% methanol, supplemented with 1% methanol after 24 h and 32 h, supplemented with 1% methanol after 48 h and 56 h, and sampled at 72 h. Obtained samples are ultrafiltration desalted and concentrated 20-fold using a ultrafiltration device with a molecular weight cutoff of 10 kDa. The treated samples are added to a buffer (20 mM citric acid-sodium citrate buffer (pH 6.6), 10 uM $ZnSO_4$). 1 µl of fermentation broth is added to 190 µl of PLC reaction solution (containing 0.5% soybean phospholipid, 25 mM citric acid-sodium citrate buffer solution pH 6.6, 10 uM $ZnSO_4$) and incubated with shaking at 45° C. for 30 minutes. After incubation, 100 μl of chloroform is added followed by oscillation mixing, centrifugation at 12000 rpm for 2 minutes. 80 μl of supernatant is taken and 20 μl of CIAP reaction solution (containing 50 mM Tris-HCl pH 9.0, 10 mM $MgCl_2$, 1 U CIAP) is added and incubated at 37° C. for 1 h. After incubation, 100 μl reaction is taken, and 900 μl of molybdenum blue development solution (containing 0.2% ascorbic acid, 0.1% ammonium molybdate) is added and incubated with shaking at 37° C. for 10 minutes. Absorbance of the samples at a wavelength of 700 nm is measured and calculated to obtain PLC activity of each broth sample. The concentration of the protein of interest is detected by SDS-PAGE electrophoretogram.

Figure 5:
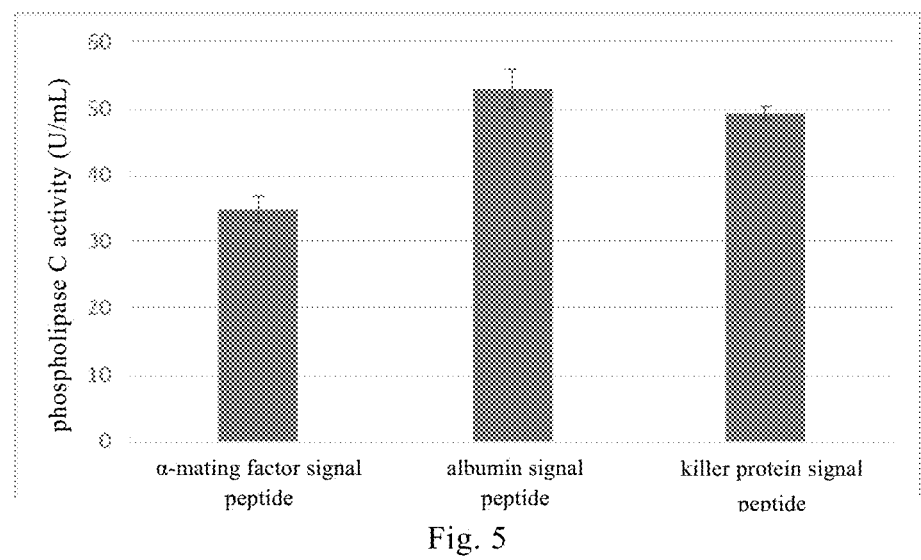
FIG. 5 shows the enzymatic activity results of BC-PC-PLC-expressing strain fermentation directed by three different signal peptides.
Figure 6:
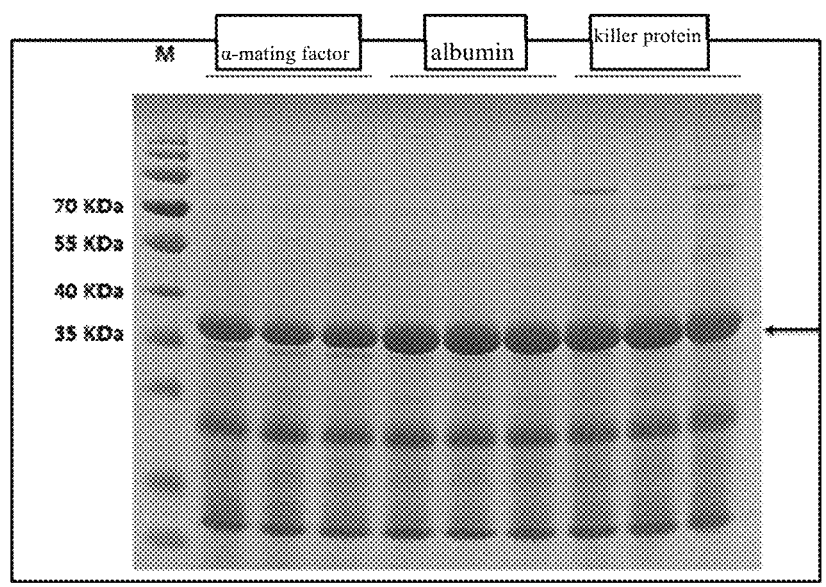
FIG. 6 shows the SDS-PAGE electrophorograms of BC-PC-PLC-expressing strain fermentation directed by three different signal peptides.

The results are shown in FIGS. 5 and 6. The amount of BC-PC-PLC expression in *Pichia* driven by albumin signal sequence from *Homo sapiens* and killer protein signal sequence from *Saccharomyces cerevisiae* is 52% and 41% higher than that by α-mating factor signal sequence, respectively.

The invention claimed is:

1. An isolated amino acid sequence having the amino acid sequence of SEQ ID NO: 7 or having the amino acid sequence having at least 95% sequence identity to the amino acid sequence of SEQ ID NO: 7,
wherein the amino acid Xaa at position 56 of SEQ ID NO:7 is Ala, Lys, Asn, Gln, His, or Trp, and
wherein in the amino acid sequence having at least 95% sequence identity to the amino acid sequence of SEQ ID NO: 7, the amino acid residue at position 63 is Asp, the amino acid residue at position 131 is Ser, the amino acid residue at position 134 is Asp, and the amino acid residue at position 56 is selected from the group consisting of Ala, Lys, Asn, Gln, His, and Trp.

2. The isolated amino acid sequence according to claim 1, wherein
the amino acid Xaa at position 56 of SEQ ID NO: 7 is alanine, asparagine, histidine or tryptophan; and/or
the amino acid sequence having at least 95% sequence identity to the amino acid sequence of SEQ ID NO: 7 has a mutation of R to H at position 20, a mutation of A to D at position 83 and/or a mutation of M to V at position 106, the amino acid residue at position 63 is Asp, the amino acid residue at position 131 is Ser, the amino acid residue at position 134 is Asp, and the amino acid residue at position 56 is selected from the group consisting of Tyr, Ala, Lys, Asn, Gln, His, and Trp; and/or the amino acid sequence comprises a signal peptide, terminal extension, GST, maltose E binding protein, protein A, tag, and/or protease hydrolysis sites for factor Xa or thrombin or enterokinase.

3. The amino acid sequence according to claim 1, wherein said amino acid sequence is selected from the group consisting of SEQ ID NOs: 4 and 6.

4. An isolated polynucleotide sequence selected from the group consisting of:
(1) a polynucleotide sequence encoding the isolated amino acid sequence according to claim 1;
(2) a complementary sequence to the polynucleotide sequence of (1).

5. A nucleic acid construct comprising a polynucleotide sequence selected from the group consisting of:
(1) a polynucleotide sequence encoding the isolated amino acid sequence according to claim 1;
(2) a complementary sequence to the polynucleotide sequence of (1).

6. A genetically engineered host cell, wherein the host cell expresses the amino acid sequence according to claim 1, or comprises a polynucleotide sequence encoding the amino acid sequence, or a nucleic acid comprising the polynucleotide sequence.

7. A composition comprising the isolated amino acid sequence according to claim 1 and optionally comprising an absorbing material.

8. An enzymatic degumming method, or a method for improving degumming performance of a phospholipase C having the isolated amino acid sequence of claim 1, wherein the method comprises: after incubating phospholipase C at a temperature between 55° C. and 75° C., adding the phospholipase C to crude oil for degumming.

9. The method according to claim 8, wherein the method has one or more of the following features:
(1) the phospholipase C is incubated at a temperature between 60° C. and 70° C.;
(2) the incubation time is 15 to 45 minutes;
(3) the enzyme is added at an amount of 50 to 1000 ppm based on the weight of crude oil;
(4) the crude oil is heated to 50 to 70° C. prior to adding the enzyme to crude oil; and
(5) the degumming comprises stirring at 50 to 60° C. for 1 to 3 hours, then heating to 80 to 90° C. and holding for 1 to 10 minutes.

10. The amino acid sequence according to claim 2, wherein, the amino acid Xaa at position 56 of SEQ ID NO: 7 is histidine or tryptophan; or in the amino acid sequence having at least 95% sequence identity to the amino acid sequence of SEQ ID NO: 7, the amino acid residue at position 56 is histidine and the amino acid residue at position 106 is valine, the amino acid residue at position 63 is Asp, the amino acid residue at position 131 is Ser, the amino acid residue at position 134 is Asp; and/or the tag is 6His or Flag, and the amino acid sequence of the signal peptide has an amino acid sequence of SEQ ID NO: 70 or 72.

11. The isolated polynucleotide sequence according to claim 4, wherein the isolated amino acid sequence is the amino acid sequence of SEQ ID NO: 7 with the amino acid Xaa at position 56 of SEQ ID NO: 7 is histidine or tryptophan; or the isolated amino acid sequence is the amino acid of SEQ ID NO: 7 with the amino acid residue at position 56 being histidine and the methionine amino acid residue at position 106 of SEQ ID NO: 7 is mutated to valine.

12. The isolated polynucleotide sequence according to claim 4, wherein the isolated amino acid sequence is selected from the group consisting of SEQ ID NOs: 4 and 6.

13. The isolated polynucleotide sequence according to claim 4, wherein the polynucleotide sequence is set forth in SEQ ID NOs: 3 or 5.

14. The nucleic acid construct according to claim 5, wherein the polynucleotide sequence is a polynucleotide sequence encoding: the isolated amino acid sequence of SEQ ID NO: 7 with the amino acid Xaa at position 56 of SEQ ID NO: 7 is histidine or tryptophan, or the isolated amino acid sequence derived from the amino acid of SEQ ID NO: 7 with the amino acid residue at position 56 being histidine and the methionine amino acid residue at position 106 of SEQ ID NO:7 is mutated to valine.

15. The nucleic acid construct according to claim 5, wherein the polynucleotide sequence is a polynucleotide sequence encoding the isolated amino acid sequence selected from the group consisting of SEQ ID NOs: 4 and 6.

16. The nucleic acid construct according to claim 5, wherein the polynucleotide sequence is SEQ ID NOs: 3 or 5.

17. The nucleic acid construct according to claim 5, wherein the nucleic acid construct is an expression vector or a cloning vector.

18. The composition according to claim 7, wherein the isolated amino acid sequence is the amino acid sequence of SEQ ID NO: 7 with the amino acid Xaa at position 56 of SEQ ID NO: 7 is histidine or tryptophan.

19. The composition according to claim 7, wherein the isolated amino acid sequence is selected from the group consisting of SEQ ID NOs: 4 and 6.

20. The composition according to claim 7, wherein the absorbing material is selected from the group consisting of activated carbon, alumina, diatomaceous earth, porous ceramics, and porous glass.

21. The composition according to claim 7, wherein the isolated amino acid sequence is the amino acid sequence of SEQ ID NO:7 with the amino acid residue at position 56 being histidine and the methionine amino acid residue at position 106 of SEQ ID NO:7 is mutated to valine.

* * * * *